(12) United States Patent
Maswadeh et al.

(10) Patent No.: US 6,672,133 B1
(45) Date of Patent: Jan. 6, 2004

(54) BIOLOGICAL CLASSIFICATION SYSTEM

(75) Inventors: Waleed M. Maswadeh, Rosedale, MD (US); Dhirajlal G. Parekh, Lutherville, MD (US); A. Peter Snyder, Bel Air, MD (US); Ashish Tripathi, Bel Air, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/205,356

(22) Filed: Jul. 25, 2002

Related U.S. Application Data

(60) Provisional application No. 60/322,828, filed on Sep. 10, 2001.

(51) Int. Cl.[7] .................... G01N 33/497; B25B 23/14; B01D 59/44; A61K 38/47

(52) U.S. Cl. .................... 73/23.34; 73/863.1; 422/83; 250/288; 424/94.6

(58) Field of Search ............... 73/23.34, 863.21; 422/83; 204/49; 250/287, 288; 424/427, 428, 94.6

(56) References Cited

U.S. PATENT DOCUMENTS

| | | | |
|---|---|---|---|
| 5,856,616 A | | 1/1999 | Maswadeh et al. |
| 5,989,824 A | * | 11/1999 | Birmingham et al. .......... 435/6 |
| 6,074,608 A | * | 6/2000 | Matz .......................... 422/83 |
| 6,446,514 B1 | * | 9/2002 | Danylewych-May et al. ............... 73/863.21 |
| 2002/0138210 A1 | * | 9/2002 | Wilkes et al. ................. 702/28 |
| 2003/0085348 A1 | * | 5/2003 | Megerle ...................... 250/287 |

OTHER PUBLICATIONS

Snyder, A., et al "Detection of the Picolinic Acid Biomarker in Bacillus Spores Using a Potentially Field–Portable Pyrolysis–Gas Chromatography–Ion Mobility Spectrometry System" Field Analytical Chem & Tech, 1(1) 49–58, 1996.

Dworzanski, J., et al "Field–Portable, Automated Pyrolysis–GC/IMS System for Rapid Biomarker Detection in Aerosols: A Feasibility Study", Field Analytical Chem & Tech. 1(5) 295–305, 1997.

Snyder, A., et al "Portable Hand–Held Gas Chromatography/Ion Mobility Spectrometry Device", Analytical Chemistry, vol. 65, No. 3, 1993.

Dworzanski, J., et al "Performance Advances in ion mobility spectrometry through combination with high speed vapor sampling, preconcentration and separation techniques", Analytica Chimica Acta 293 (1994) 219–235.

Snyder, A., et al "Portable, hand–held gas chromatography ion mobility spectrometer" American Laboratory, 32B–32H (1992).

* cited by examiner

Primary Examiner—Hezron Williams
Assistant Examiner—Jay L Politzer
(74) Attorney, Agent, or Firm—Ulysses John Biffoni

(57) ABSTRACT

A hand-held chemical vapor detector for detecting biological substances in an indoor and outdoor setting is claimed. More specifically, the present invention relates to a plasma chromatograph (PC) vapor detector that is interfaced to a biological sample processing and transfer introduction system. The biological sample processing was accomplished by quartz tube thermal decomposition (TD), and the resultant vapor was transferred by gas chromatography (GC) to the PC detector. This system is comprised of a thermal decomposition module, gas chromatography module and a plasma chromatograph detector. These components are connected in a series fashion. The device is referred to as a Biological Classifier System (BCS). The BCS can be described as a hyphenated device where two analytical dimensions (the GC and PC), in series, allow the separation and isolation of individual components from the thermal decomposition of biological analytes.

33 Claims, 15 Drawing Sheets

D/d = 4

D/d =10

D/d = 20

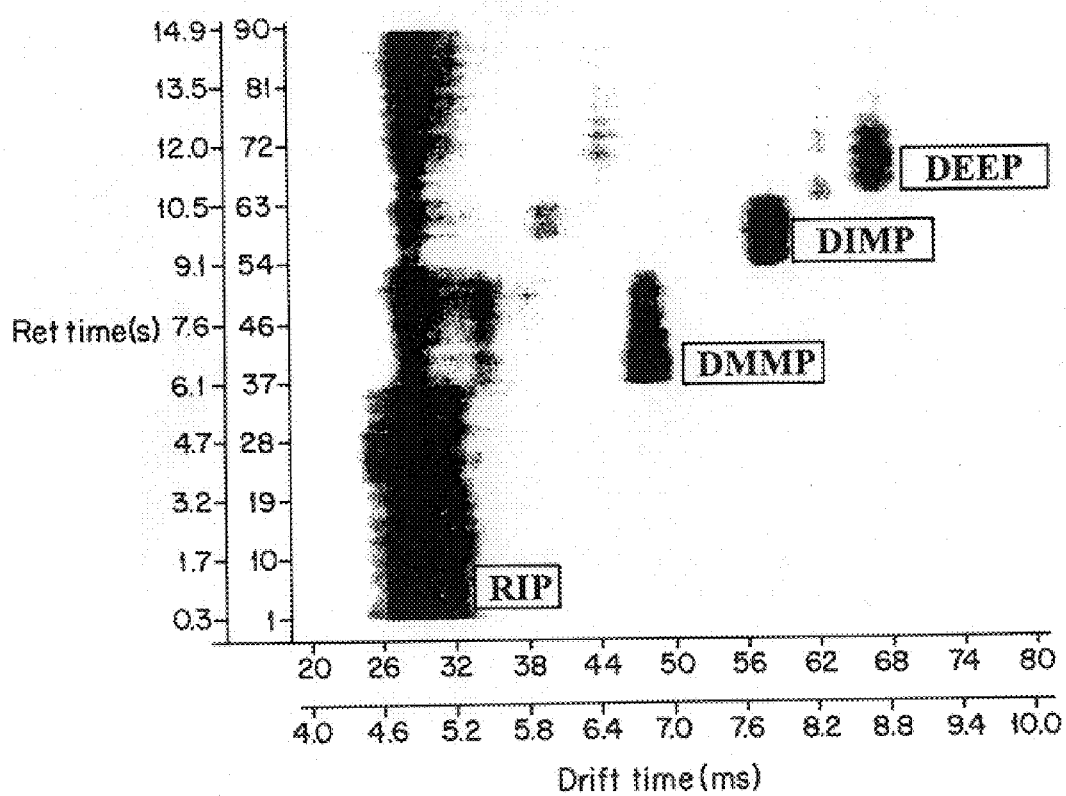

BIOLOGICAL CLASSIFICATION SYSTEM

REFERENCE TO RELATED APPLICATIONS

This application claims the benefit of provisional application Ser. No. 60/322,828 filed Sep. 10, 2001 which is hereby incorporated by reference as if specifically set forth herein.

GOVERNMENT INTEREST

The invention described herein may be manufactured, used and licensed by or for the U.S. Government.

BACKGROUND OF THE INVENTION

1. Field of the Invention

The present invention relates to a hand-held chemical vapor detector for detecting biological substances in an indoor and outdoors setting. More specifically, the present invention relates to a plasma chromatograph (PC) vapor detector that is interfaced to a biological sample processing and transfer introduction system. The biological sample processing was accomplished by quartz tube thermal decomposition (TD), and the resultant vapor was transferred by gas chromatography (GC) to the PC detector. This system is comprised of a thermal decomposition module, gas chromatography module and a plasma chromatograph detector. These components are connected in a series fashion. The device is referred to as a Biological Classifier System (BCS). The BCS can be described as a hyphenated device where two analytical dimensions (the GC and PC), in series, allow the separation and isolation of individual components from the thermal decomposition of biological analytes.

2. Brief Description of Related Art

Recent and current events around the world have highlighted the possibilities for deliberate outdoor dissemination of harmful biological substances, and at least 12 countries are known to have some degree of biological warfare program capabilities. Alleged biological terrorism attacks in Japan and threats on U.S. domestic commercial establishments have increased significantly in the past five years. Reports of alleged localized aerosol releases and hoax domestic biological terrorism in the form of postal mail packages, allegedly with spores of the pathogenic *Bacillus anthracis* and *Yersinia pestis* (bubonic plague) organisms, serve to exacerbate the problem.

Desirable goals in effectively countering the biological warfare and terrorism applications of harmful biological agents include their ready detection and possible identification in a relatively short period of time. The detection of biological aerosols, particularly that of bacterial cells and spores, is an important component of U.S. military biological programs. A portion of these programs consists of analytical instrumentation to effect trigger, detection, and identification responses for the presence of bacterial aerosols.

Analytical investigations of aerosols have relied on a diverse set of approaches over the last three decades from experimental determinations of generated aerosols from bulk solutions to real time analyses of ambient outdoor particles. These investigations have included inorganic (salts) and organic particulates as well as bioaerosols that include microorganisms, fungi, and pollen. An accounting of the most prevalent techniques and instrumental methods appears constructive with respect to the present analytical detection method of biological aerosols.

Traditional methods for the characterization of aerosols consist of sampling ambient air and collecting/concentrating them on various matrices (1–3). These biological aerosol particulates are then subjected to sample detection techniques such as polymerase chain reaction (PCR) (1,2,4,5), colony plate count or most probable number (MPN) (1,4,6, 7), bioluminescence from inherent adenosine triphosphate (ATP) (4,8), phase-contrast microscopy (4), and immunoassay (1,4,9). The bacterial aerosol samples were characterized by these traditional detection techniques in either an off-line or on-line fashion.

*Pseudomonas fluorescens* bacteria were aerosolized and directed to an agar plate with a laser sizing system placed after the aerosol generator. This was an important development in that a relation could be produced between the total number of particles and the number of bacterial-colony-forming units on the agar growth plate (10).

Mass spectrometric methods have had a long and rich history as analytical vehicles for investigating compositional properties of artificial and outdoor man-made aerosols as well as ambient organic and inorganic aerosols under off-line or on-line analysis conditions.

Laser microprobe mass analysis (LAMMA) has been used in an off-line fashion to investigate aerosol particles. Particles were collected or placed on a matrix or wire mesh and were introduced into a vacuum. A microscope guides a laser beam to a selected particle or spot on the matrix surface where ions desorb and are analyzed by a time-of-flight mass spectrometer (TOFMS). Relatively low molecular weight species were usually observed, and known species mostly represented the inorganic salt fraction of samples such as *Mycobacterium leprae* (11,12), *B. anthracis*. *B. thuringiensis,* and *B. cereus* (13,14) as well as ionized species of particulates including polyaromatic hydrocarbons (PAH) (15) and salt species. Two recent review articles on LAMMA document the principal and extensive applications of TOF and Fourier-transform mass-spectrometer analyzers in the analysis of laser generated ions of single aerosol particles (17,18) that were placed or impacted on matrix supports.

The TOFMS field evolved to where an aerosolized suspension of biological particulates could be introduced into a vacuum as single particles. This procedure, particle analysis by mass spectrometry (PAMS), used either a hot rhenium filament to pyrolyze individual bacterial particles (19–22) or a laser to desorb and ionize species from particles (22,23). These biological particles, including *Pseudomonas putida, Bacillus cereus,* and *Bacillus subtilis* var. *niger* were generated from an ethanol-water suspension. Linear quadrupole mass spectral determinations mainly produced unknown pyrolysis fragments and inorganic salt-derived species.

A similar system, developed by Gieray, Reilly, Yang, Whitten, and Ramsey (24) used an ion trap mass spectrometer detector. From a bulk water suspension, bacterial aerosol particles were sensed and a trigger was provided by the particles passing through two argon ion laser beams. An excimer laser ablated the particle in the ion trap so as to produce ions. An improvement on this basic design was that of a TOF system (25–27) replacing the quadrupole mass spectrometer designs. This allowed for faster mass spectral scanning of ions from particles generated from bulk suspensions or directly from laboratory ambient air. Salt particles as well as tobacco smoke and soot were analyzed.

Hars et al. used a combined electrodynamic balance/ion trap mass spectrometry technique for trapping and stabilizing aerosolized particles of polystyrene and *Bacillus subtilis* spores, followed by laser fragmentation/ionization to obtain mass spectra of the ions generated during a 450-mJ pulse from a Nd-YAG laser. They demonstrated the feasibility to use this technique for chemical and physical characterization of single cells of microorganisms and other components of respirable aerosols (28,29). In other work, an aerosol particle-sizing laser was interfaced to a laser thermal desorption/ionization beam for TOFMS analysis on organic and inorganic compounds (30,31).

Prather et al. published a series of evolving articles with the concept of size, aerodynamic diameter, chemical composition and composition class, and temporal characterization of outdoor aerosol particles (32–39). The centerpiece was a transportable aerosol concentrator, dual time-of-flight mass spectrometer. Positive ions are analyzed in one tube and negative ions, from the same particle, are analyzed in the second time-of-flight tube. As an example, over a period of four days, pyrotechnic explosives (fireworks) particles were monitored in the atmosphere: monitoring sites were 0.5 and 3 miles from the explosion sources (37). Further examples of this technology are the characterization of automobile emissions (36) where metals, oxides, hydroxides, and polyaromatic hydrocarbons (PAH) were detected, and in the temporal monitoring of the nitric acid to hydrochloric acid heterogeneous chemistry that occurs in atmospheric aerosols over the ocean-land mass interface (39).

Gas chromatography (GC)-MS has been used for the trace analysis of bacteria and fungi in organic dust aerosols from environments such as hospitals and homes (40–44) and biotechnology processes (45,46). The air was continually sampled for bacteria for a period of 24 h, and the bacteria on the filter were processed for the extraction of specific biochemical compounds for GC-MS analysis.

Biological aerosol analyses using analytical instrumentation were mainly relegated to controlled investigations in laboratory settings as related earlier. Only a few investigations can be found in the literature concerning the real-time detection of bacterial aerosols in outdoor scenarios, and the detection methods were primarily spectroscopic in nature. Real-time detection of Bacillus spore aerosols from the dissemination of bulk suspensions in outdoor testing areas was accomplished by a light detection and ranging (LIDAR) system. This is a remote detection system where a 1064-nm laser beam was used to interrogate a *Bacillus subtilis* var. *niger* aerosol plume approximately perpendicular to the beam (6,47). The backscattered radiation was collected by receiver telescope optics and used in the determination of bacterial aerosol presence.

The fluorescence of an aerosol of *B. subtilis* from bulk suspension was detected as single particles with a fluorescence particle-counter instrument in outdoors and under indoor, controlled conditions. An argon laser beam of 488 nm interrogated a beam of particles by monitoring emission in the 530 to 550-nm range (48,49). Flavin compounds in the bacteria were surmised, because the bacterial component responsible for the emission at 530 to 550 nm and non-biological interferences displayed no fluorescence activity in the emission bandwidth. Another report dealt with combining the 488-nm argon laser, which produces size-scattering and visible fluorescence, with a 266-nm pulsed laser to produce 300–500-nm UV-VIS fluorescence of the proteinaceous bacterial components (50) from the generated aerosols. Similar experiments with *B. subtilis* were shown with a 325-nm helium-cadmium laser excitation source with fluorescence monitoring at 420 to 580 nm (51).

The first TD-GC-PC analyses of biological materials, including Bacillus spores and nucleic acids, appear to have been reported by Meuzelaar, Kim, Arnold, Kalousek and Snyder (52). This was followed by systematic TD-GC-PC studies of various biopolymers relevant to bioagent detection (53) as well as potential interferences, culminating in a recent PhD thesis by Thornton (54).

Prototype portable GC-PC concept systems were shown to successfully separate headspace vapors from complex liquid mixtures of analytes (55–57).

Laboratory testing of the prototype of the currently fielded TD-GC-PC version was performed under controlled sample introduction of bacterial suspensions (58). Moreover, a preliminary presentation of a spore aerosol investigation in the field with the prototype TD-GC-PC was reported recently (59). Finally, a more comprehensive study of the detection of outdoor aerosols of *Bacillus subtilis* var. *niger* (BG) bacterial spores, Gram-negative *Erwinia herbicola* (EH) bacteria and ovalbumin protein with TD-GC-PC has recently been performed (60–62).

Technologies are very different from TD-GC-PC and can produce better or less information. Almost all have not been tested in the field and some are large and are a logistics burden.

The present investigation provides for the determination of desirable properties of generated biological aerosols.

SUMMARY OF THE INVENTION

A biological classification system that is made of a thermal decomposition tube for processing a biological sample and producing a resultant vapor, a gas chromatography module interfaced with the thermal decomposition tube by a three-way injection valve, the gas chromatography module for receiving the resultant vapor from the thermal decomposition tube, and a plasma chromatograph vapor detector interfaced via a GC/PC interface with the gas chromatography module for receiving resultant vapor from the gas chromatography module. In the biological classification system of the present invention, the thermal decomposition tube, the gas chromatography module and the plasma chromatograph vapor detector are connected in series for separation, isolation and classification of individual components from the thermal decomposition of biological analytes introduced into the thermal decomposition tube.

BRIEF DESCRIPTION OF THE FIGURES

FIG. 12 is a graph of the GC-PC dataspace of an experiment with the three listed chemicals. DMMP, DEMP and DIMP are separated in GC and PC analytical dataspace. The RIP is the reactant ion peak, and that is protonated water.

DETAILED DESCRIPTION

A commercially available, hand-held chemical vapor detector was modified to detect biological substances such as Gram-positive Bacillus spores, Gram-negative vegetative organisms and proteins in outdoor field scenarios. A plasma chromatograph (PC) vapor detector was interfaced to a biological sample processing and transfer introduction system. The biological sample processing was accomplished by quartz tube thermal decomposition (TD), and the resultant vapor was transferred by gas chromatography (GC) to the PC detector. This system is comprised of a thermal decomposition module, gas chromatography module and a plasma chromatograph detector. These components are connected in a series fashion. The device is referred to as a Biological Classifier System (BCS). The BCS can be described as a hyphenated device where two analytical dimensions (the GC and PC), in series, allow the separation and isolation of individual components from the thermal decomposition of biological analytes.

Objectives a. The BCS was designed to detect the presence of ambient biological and non-biological (i.e.—chemical) aerosols from an aerosol concentrator.

b. The BCS can accept and detect biological and chemical substances in liquid matrices by simple syringe injection into the system.

c. The BCS can accept and detect vapors and gases by direct introduction into the TD source.

d. The system was designed to operate in a laboratory, indoor or in outdoor field conditions while sampling the air for the detection (trigger/detect/classify) of chemical and biological aerosol particles and gases/vapors in the atmospheric air.

Description and Operation

Figure 1A:
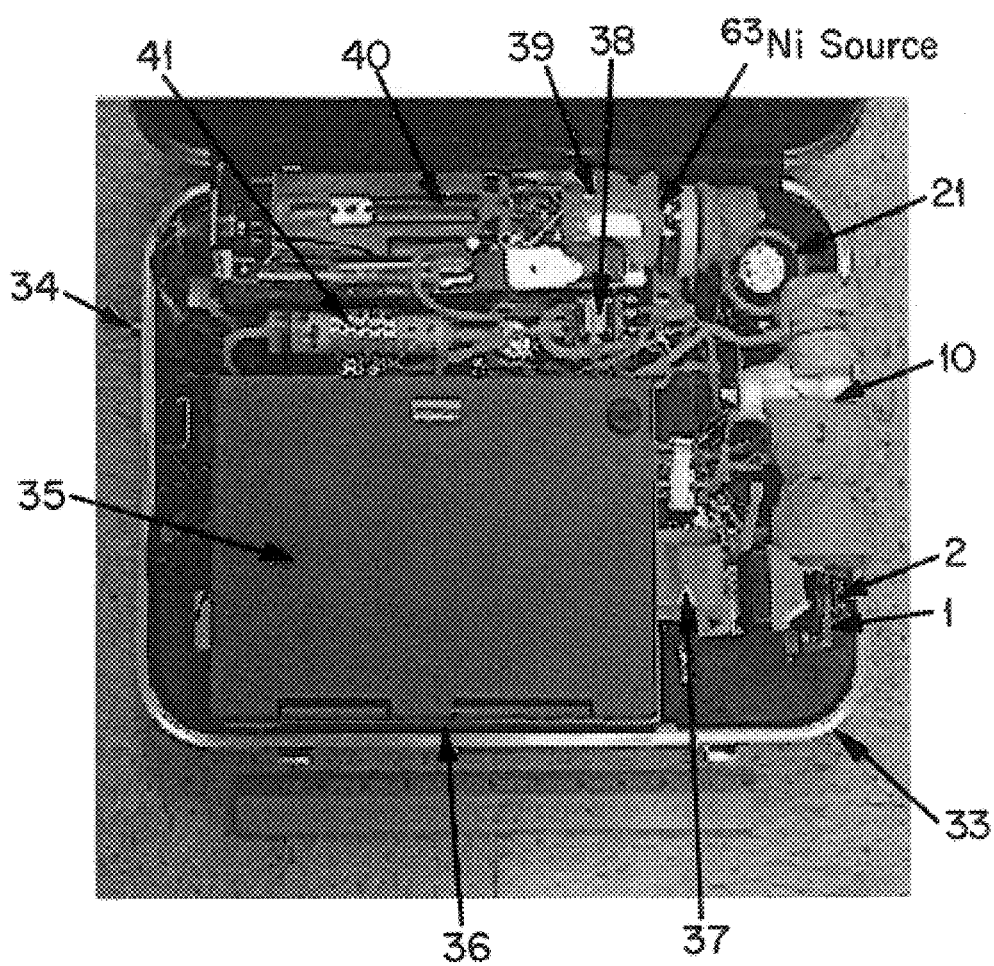
FIG. 1A is a photograph of the Biological Classifier System according to the invention.

Various models of a TD unit were designed and tested and a digital picture of the device is shown in FIG. 1A. The features of the device shown in FIG. 1A are a briefcase 33, computer 35, 15 VDC Power Input 34, electronic hardware 36, 50-pin Cable to PCMCIA card 37, vacuum pump 38, PC Cell 39, PC sieve pack 40, Sieve Packs 41, GC Injection valve 10, thermal decomposition tube 2 and aerosol inlet 1.

Figure 1B:
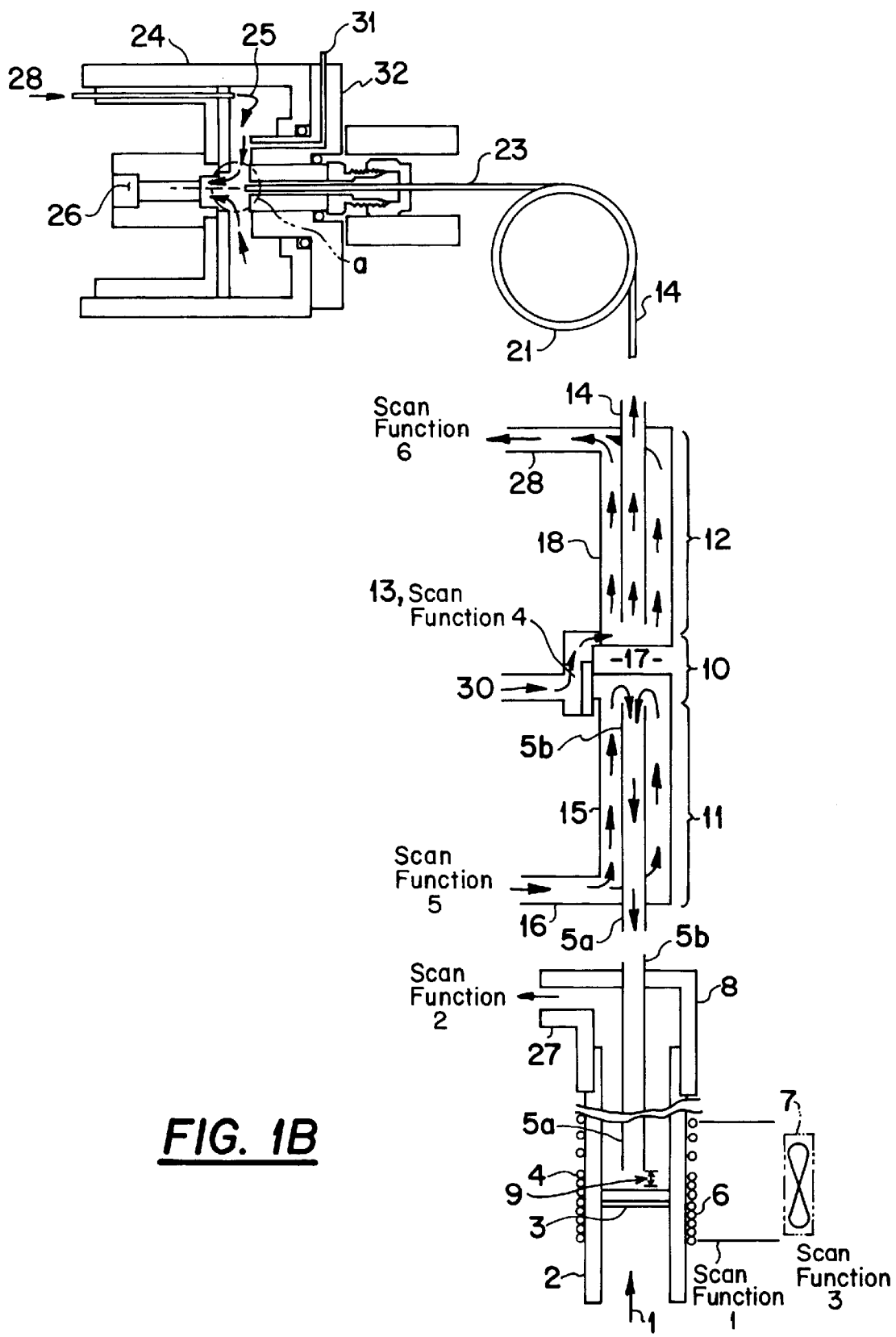
FIG. 1B is a schematic representation of the thermal decomposition tube, the gas chromatography module and the plasma chromatograph vapor detector connected in a series fashion.
Figure 11:
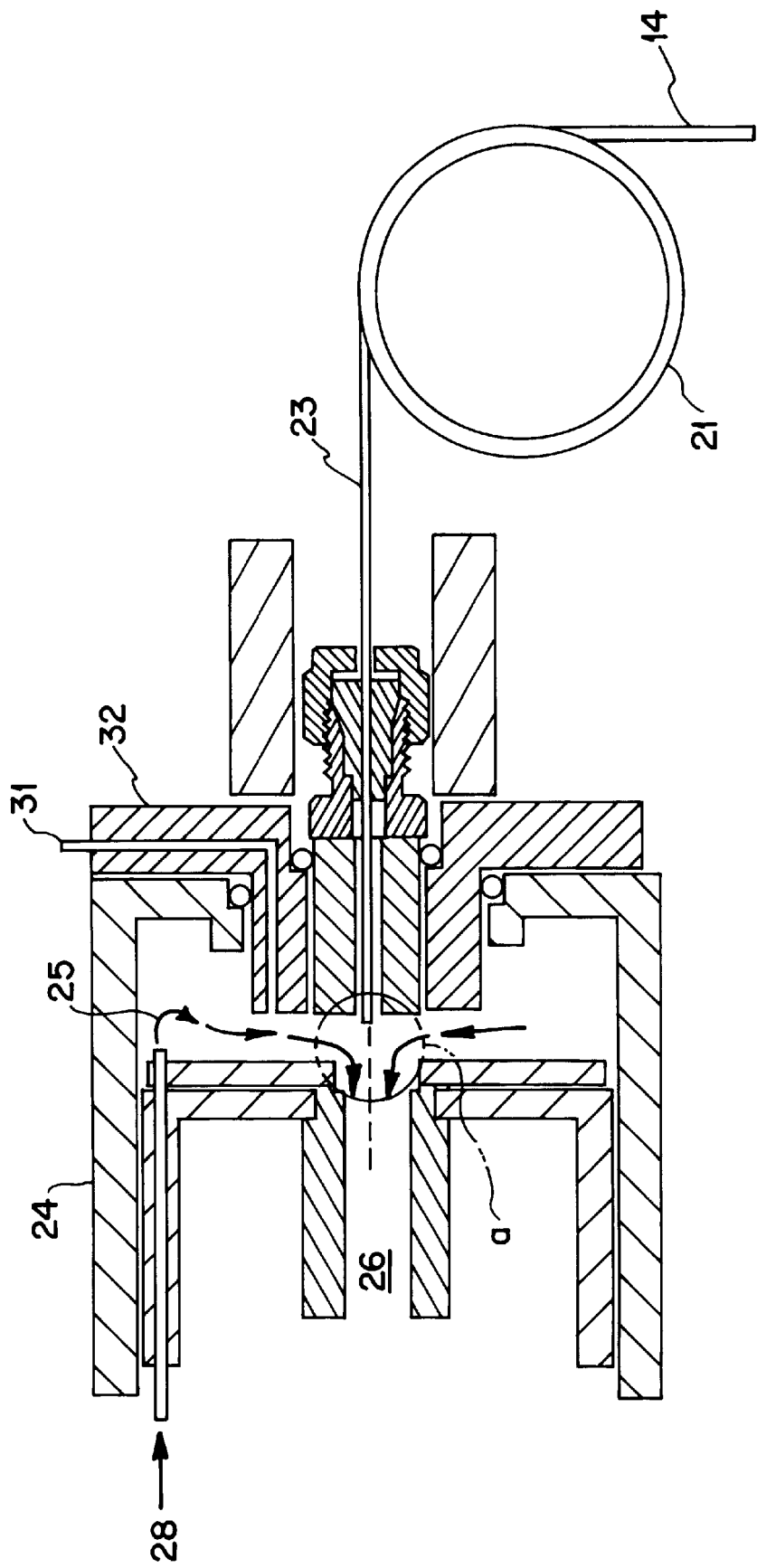
FIG. 11 is a cross-section diagram of the interface between the GC and the PC.
Figure 13A:
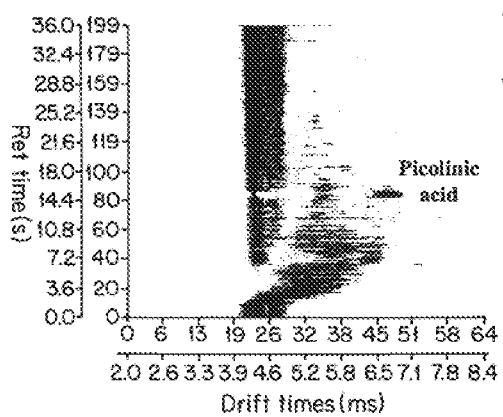
FIGS. 13A–D is a graph of the TD-GC-PC experiment of *Bacillus subtilis* spores. Note that the signal is derived from the inherent picolinic acid compound found in Gram-positive spores. Bacillus spores contain 5–15% by weight of dipicolinic acid; picolinic acid is a common TD product of dipicolinic acid. This biochemical compound is very sensitive to the Ni-63 ionization in the ion source of the PC.
Figure 13B:
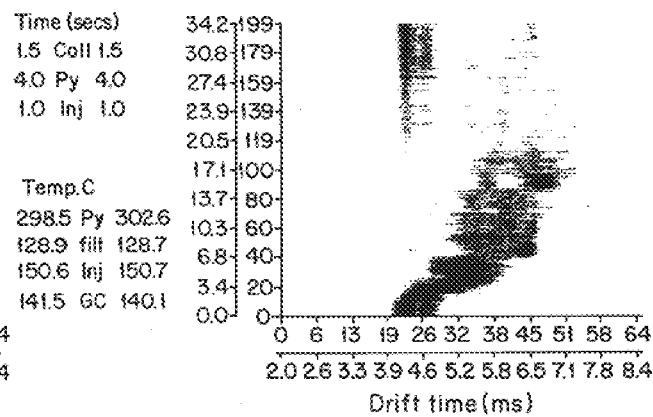
Figure 13C:
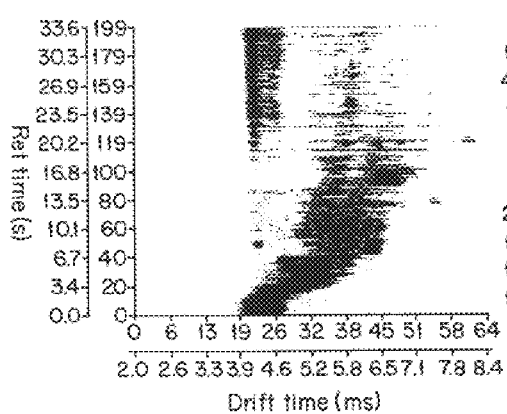
Figure 13D:
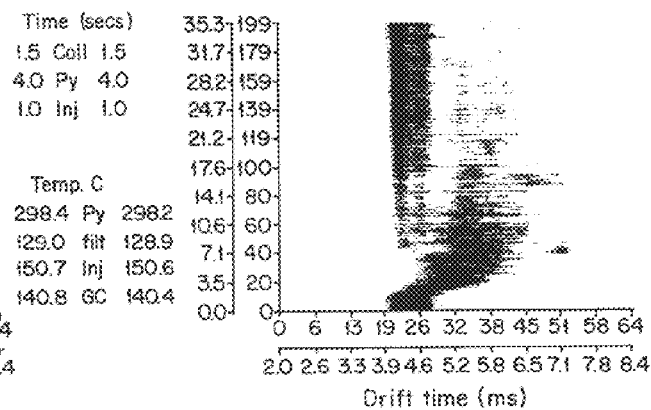

FIG. 1B shows the complete device, including the thermal decomposition tube (also shown in FIG. 2), three way valve 10 (shown in FIGS. 5A and 5B), GC ring (shown in FIG. 8), and PC Cell (shown in FIG. 11).

FIGS. 2–10 provide schematics and operational diagrams of the BCS system.

Figure 2:
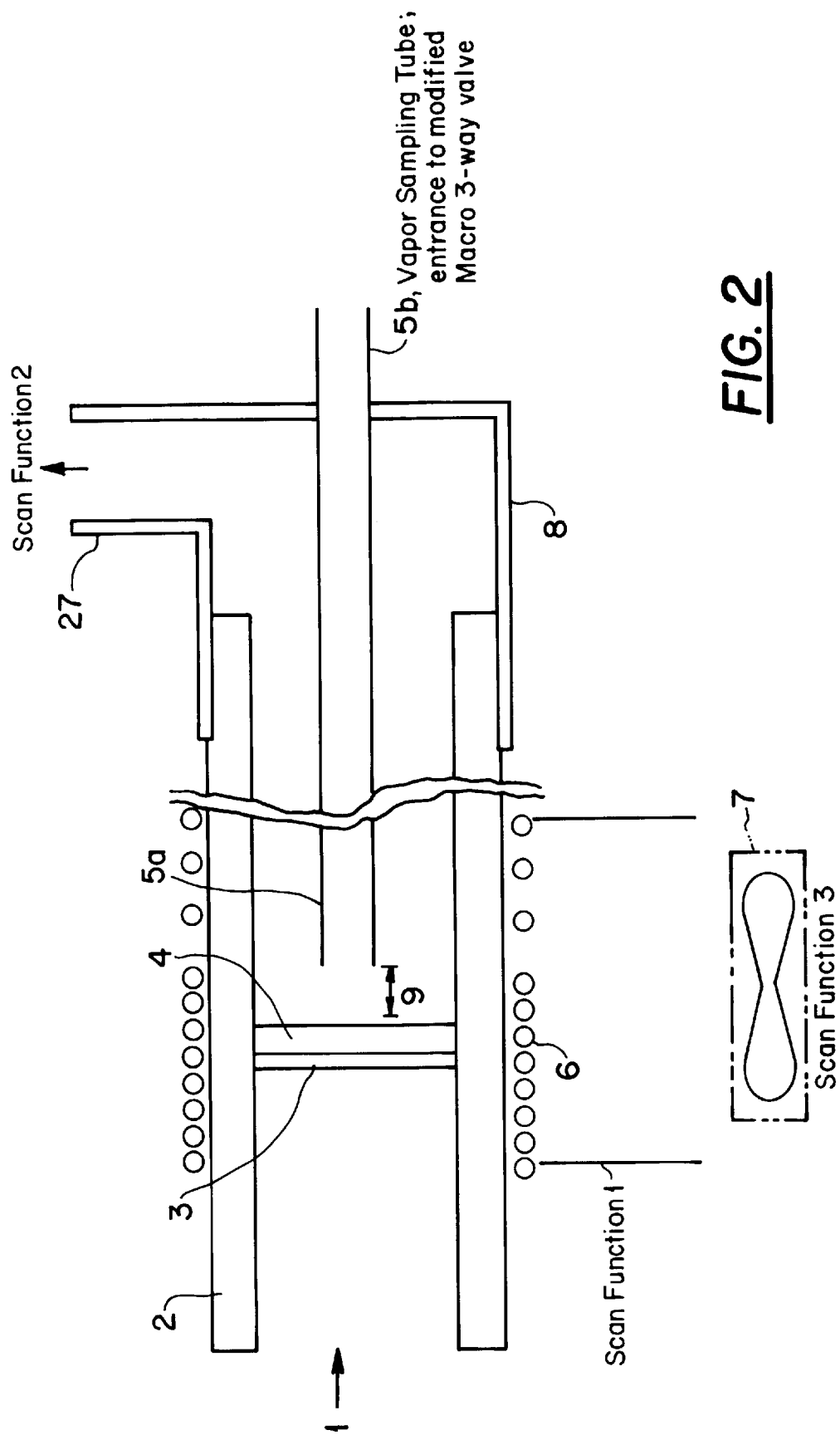
FIG. 2 is a schematic representation of the features of the sample introduction TD area.

FIG. 2 is detailed as follows. A sample is introduced into the entrance 1 of the Pyrex thermal decomposition tube 2 and deposited (solid, liquid) or passed through (vapor) the replaceable (expendable) micro fiber filter 3. The preferred TD unit consists of a Pyrex TD tube 2 that is preferably ¼ inch OD×4 mm ID×50 mm long; a replaceable high-temperature aerosol retaining filter 3, preferably, a quartz micro-fiber filter; a permanently fixed quartz frit 4; fused silica glass-lined stainless steel tube, also referred to as a vapor sampling tube, preferably 1/16 inch OD×0.02 inch ID×3.65 inch long 5. Tube 5 connects the TD source to the modified macro 3-way valve (see FIG. 5); the vapor sampling tube entrance is 5a and the vapor sampling outlet is 5b; heating element or heating wire 6 that is controlled by scan function 1, (see FIG. 3); the airflow rate and time period required to change the airflow rate through the Pyrex TD tube from high to low and vice versa is controlled by scan function 2; cooling fan assembly 7 that is controlled by scan function 3, (FIG. 3); and interface housing 8 that accurately positions the vapor sampling tube entrance 5a to the frit 4, and the Pyrex TD tube vent 27.

Different aerosol retaining filters 3 were investigated and the preferred filter 3 is a high-temperature, quartz micro-fiber filter (QMA-100, Whatman), which is replaceable. All internal surfaces in the TD source are inert and made of glass material. The distance and the position 9 of the vapor sampling tube entrance 5a to the quartz frit 4 is very critical and is positioned to permit maximum transmission of the thermal decomposition products, to provide low dilution volume (dead volume), and to minimize surface contact on any surrounding cold spots. Various distances (0.1–25 mm) were investigated and the preferred distance is 2 mm. Various vapor sampling tube 5 types as well as sizes were used and the preferred tube 5 is a 1/16×0.02×3.65 inch glass-lined stainless steel tube 5. The quartz frit 4 has an internal pore size of 200 microns while the thickness is set to a preferred 1 mm thick. Frits with pore sizes greater than 200 um tend to admit thermally decomposed particulates that can clog the GC column. Smaller pore sizes result in very low airflow through the system. Frits thicker than 1 mm retain some of the vapor compounds and thinner frits are too fragile and break apart. Unacceptably high internal pressures would be required in order to pass the vapor through a frit thicker than 1 mm.

Figure 3:
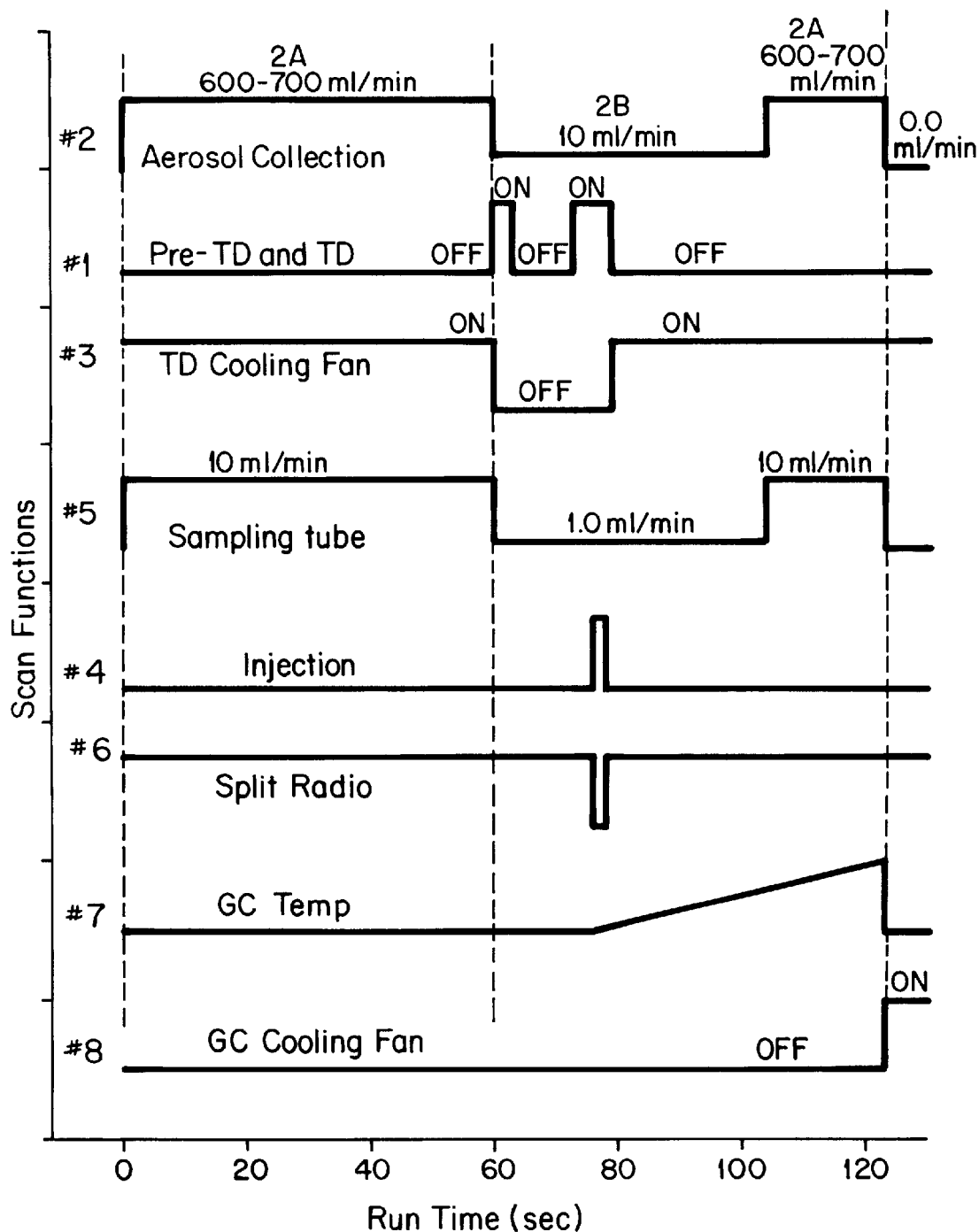
FIG. 3 is a graph showing the scan functions of the process for one cycle with 1-minute aerosol collection.

Various TD heating wires 6 and coiling styles were tested. The preferred TD heating wire is 0.013-inch OD Alomega wire, which has a low total thermal mass capacity and a heating rate that reaches 700° C. in 2–3 seconds. The heating wire 6 is coiled in a manner that permits the right amount of heat deposition over the upstream and down stream regions of the filter/frit (3/4). The preferred style of coiling the heating wire 6 is depicted in FIG. 2 where the coil winding density is higher about the filter/frit (3/4) region than that about the entrance of the vapor sampling tube entrance 5a tip region. The vapor sampling tube is positioned 2 mm from the quartz frit, and this is a compromise position to prevent too little or too much vapor from entering the tube. The heating wire is controlled by scan function 1, (FIGS. 2 and 3). The scan function produces a maximum of primary vapor products with minimal post degradation and secondary vapor products. The cooling fan assembly 7 is used to quickly cool the heated TD region for the next analysis.

Figure 4A:
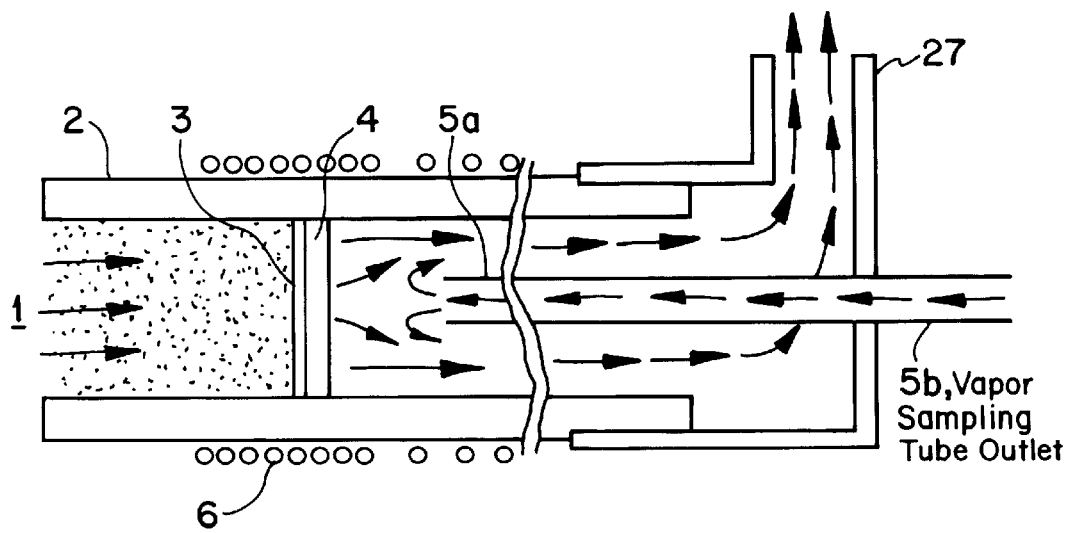
FIGS. 4A–4C are schematic representations of the flow of air through the sample introduction system under the control of various scan functions.
Figure 4B:
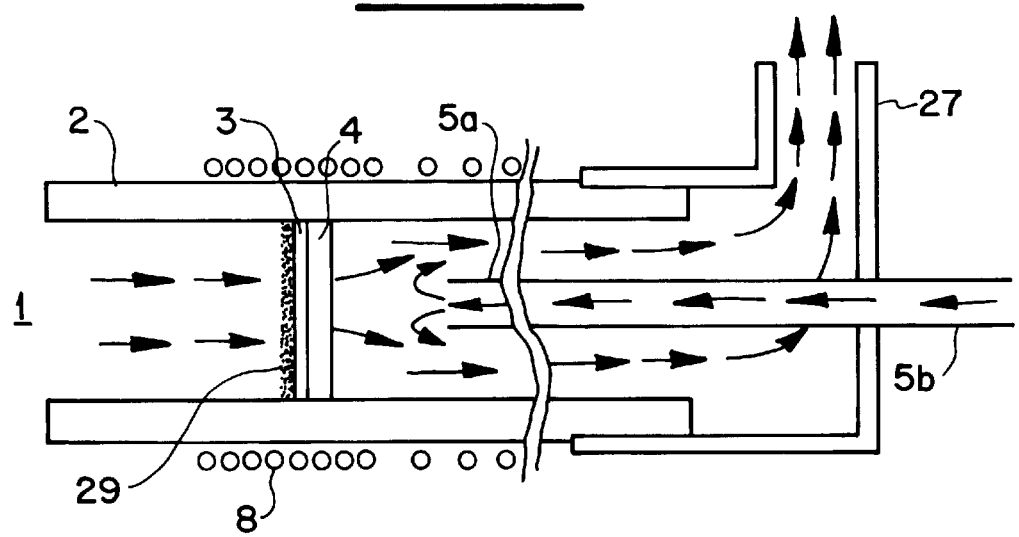
Figure 4C:
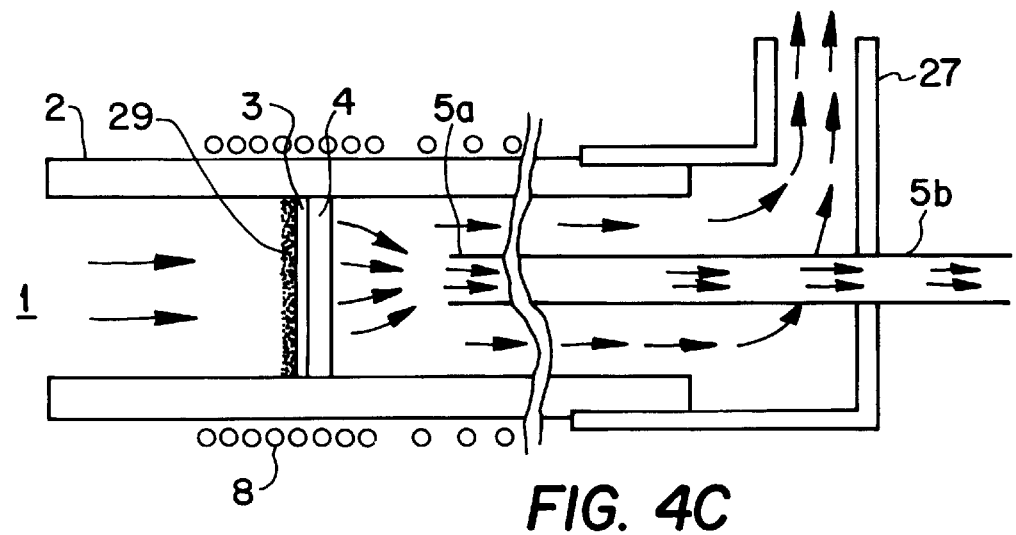

Another factor in the TD unit is the airflow switching/control scan function 2. FIGS. 4A–C show the airflow direction during various stages of scan function 2. FIG. 4A shows the first stage of scan function 2 (scan 2A) where aerosol enters the heating source entrance 1 (FIG. 3) and encounters the quartz micro-fiber filter 3. Aerosol particulates 29 are trapped and retained by the filter 3 (FIG. 4B) during scan function 2A (FIGS. 3 and 4A). The vapor sampling tube 5 is flushed and cleaned by clean dry air that flows counter-current to the major airflow. Thermal decomposition does not occur at this point. During aerosol collection, the preferred airflow rate through the TD tube 2 is 700 ml/min. Airflow rates from 0–2000 ml/min were investigated and the preferred airflow rate was observed to be 700 ml/min. When airflow of 700-ml/min is going through the TD tube 1, the preferred airflow rate through the vapor sampling tube 5 is 1 ml/min. FIG. 4B shows the second stage (sample processing/thermal decomposition) of scan function 2 (scan 2B, see FIG. 3) where the aerosol has been deposited on the filter paper. Thermal decomposition of the sample occurs. The airflow rate through the TD tube 2 is reduced significantly from 700 ml/min to a preferred value of 10 ml/min. The vapor sampling tube 5 is kept clean by a countercurrent airflow (arrows) during aerosol collection (FIG. 4A) and thermal decomposition (FIG. 4B). Airflow rates, so as to sweep the thermal decomposition vapor products efficiently through the TD tube 2, were investigated from 0–100 ml/min, and the preferred rate is 10 ml/min. FIG. 4C shows the airflow rate through TD tube 2 and vapor sampling tube 5 during the sample injection pulse. The preferred airflow rate through the vapor sampling tube 5 to produce an efficient injection of thermal decomposition vapors is 27 ml/min. Vapor injection airflows between 1–200 ml/min were investigated, and 27 ml/min was the preferred sample injection airflow rate into the vapor sampling tube 5.

Scan function 1 in FIG. 3 shows two events. The first, shorter in time event is the pre-TD or drying stage. This stage dries the solid particulates that were collected onto the filter paper. The second, longer in time event is the thermal decomposition event. After 4 seconds, the vapor is injected into the vapor sampling tube entrance 5a in FIG. 4. The event is shown as scan function 4 in FIG. 3. Thus, the difference in time between the initiation of thermal decomposition (second event in scan function 1) and the initiation of the injection event (scan function 4) is 4 seconds.

Scan function 4 in FIG. 3 shows the absolute duration of the vapor injection pulse into the vapor sampling tube entrance 5a as 2 seconds.

The heating event is terminated at 6 seconds after initiation of thermal decomposition. The temperature in the quartz tube reaches 350° C. in the first 5 seconds. These conditions yield a maximum of TD vapor products in the shortest time.

Certain criteria in the above discussion are important to provide for a satisfactory thermal decomposition. These are not mentioned in the published open literature. The improvements over the prior art are as follows:

The heating wire is coiled in to obtain more winding about the quartz filter 3 region compared to fewer windings about the vapor sampling tube 5.

The pore size and thickness of the quartz frit 4 is 200 um and 1 mm, respectively.

The vapor sampling tube entrance 5a is positioned 2 mm behind the quartz frit 4.

During thermal decomposition and injection of the vapor sample, the airflow rate is maintained at a preferred 10 ml/min to reduce the residence time of the vapor products inside the thermal decomposition region. Airflow rates from 0–100 ml/min were investigated, and 10 ml/min is the preferred value. This airflow rate was optimized to allow maximum production of primary vapor compounds and minimum production of secondary degradation products. The vapor generated or passing through the quartz frit enters the vapor sampling tube 5a, exits the vapor sampling tube 5b, and enters the 3-way valve 10 at 4 seconds after the TD event. The injection pulse has an absolute time span of 2 seconds. The TD heating event reaches 350° C. in the first 5 seconds and at 6 seconds the heating is turned off. These conditions yield a maximum of TD vapor products in the shortest time period. This optimization can be found in the Aug. 15, 2001 published paper in Rapid Communications in Mass Spectrometry, volume 15, pages 1672–1680 (Aug. 15, 2001) in FIGS. 3 and 4 in that paper, incorporated herein by reference in its entirety.

The preferred sample injection flow rate into the vapor sampling tube entrance 5a is 27 ml/min.

This airflow rate optimization allows for a maximal amount of primary vapor products to pass through the quartz frit, vapor-sampling tube, and into the 3-way injection valve region 10 (see FIG. 5) while minimizing the amount of primary vapor products that continue to be heated. Continual heating of the primary vapor products produces secondary vapor products. This secondary thermal decomposition phenomenon destroys the primary vapor products by breaking them up into smaller compounds (secondary vapor products), and the secondary vapor products provide no useful detection/classification information.

The next section of the BCS details the 3-way macro injection valve. Details of the 3-way macro injection valve have not been disclosed in the open literature reports.

The high temperature 3-way macro injection valve 10 for vapor sample injection into the GC is composed of the inlet 11 and outlet interface 12 that allow (FIG. 5) a normally large (macro) valve 10 to operate as a 3-way micro-valve. The resulting 3-way microinjection valve is actually a modified 3-way macro injection valve. The relatively large dead volume of 150 microliters in a conventional valve is reduced to a volume in the low nanoliter range by the modifications to the macro valve. The inlet 11 and outlet 12 interfaces were designed to virtually eliminate the dead volume and memory effects. The vapor sampling tube outlet/injector (5b/10) interface was designed (FIG. 5) to allow the shortest distance between the vapor sampling tube outlet 5b and the injector orifice valve 13. The distance between the vapor sampling tube outlet 5b and the injector orifice valve 13 is 2 mm. During the non-injection, non-sampling period (FIG. 5A, airflow arrows in the inlet interface 11), the surrounding 10 ml/min purge flow is activated and valve 13 is closed. Scan function 6 allows the airflow to enter the injector airflow inlet 30, continue into the GC entrance 14, and exhaust out through the outlet branch airflow exit 28. During the injection (sampling) period (FIG. 5B), valve 13 is opened, and the surrounding purge flow is set to zero to allow maximum vapor sample transfer through the injector orifice.

The outlet interface 12 is designed (FIG. 5) to allow the shortest distance between the GC entrance 14 and the injector orifice valve 13 with a surrounding airflow to purge the interface volumes (arrows in outlet interface 12).

This interface produces a minimum distance for the sample to travel from the entrance of the vapor sampling tube 5 to the GC inlet 14.

Modifications were made to a commercial macro 3-way valve to reduce the dead volume from 150 microliters to the low nanoliter range. A macro (commercial) high temperature 3-way valve 10 was modified and transformed to perform as a genuine 3-way micro-valve by adding an inlet 11 and an outlet interface 12 as depicted in FIG. 5.

This new design offers the following unique features for the sample injection valve 10: a) The two interfaces 11 & 12 offer fast flushing and cleaning of internal volumes with no or negligible memory effect. b) The interfaces 11 and 12 provide minimum distance and minimum volume between the vapor sampling tube outlet 5b and the GC inlet 14. c) Electronic circuits in the electronic control board and air flow plumbing (FIG. 6) are used to control the airflow rate and the time it takes to change the airflow rate from low to high and vice versa for both interfaces 11 and 12.

The preferred ratio of sample airflow into the GC inlet 14 to waste airflow venting out through the outlet branch airflow exit 28 (FIG. 5B) is 90:10 upon sample injection into the GC column 14 for PC detection.

Figure 5A:
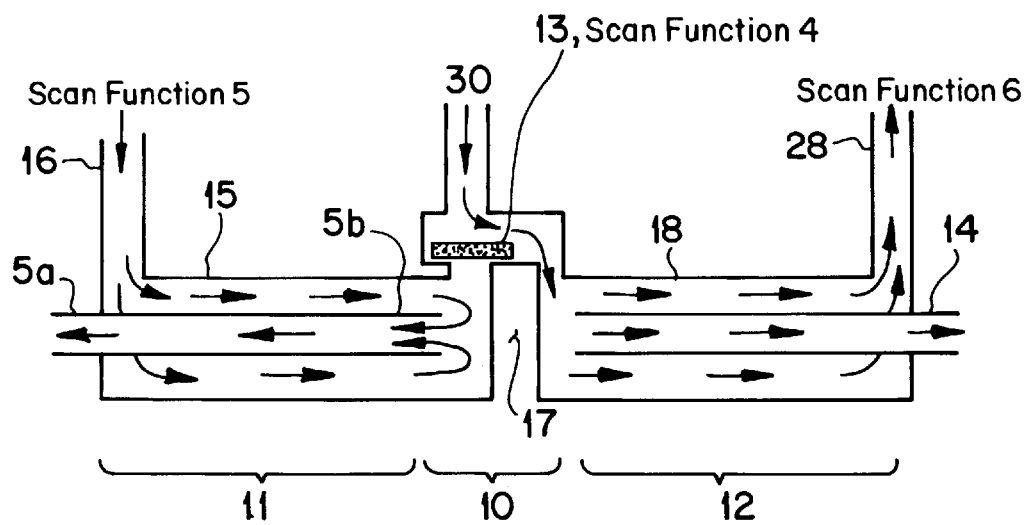
FIGS. 5A–5B are schematic representations of the flow of air through three-way injection valve region.
Figure 5B:
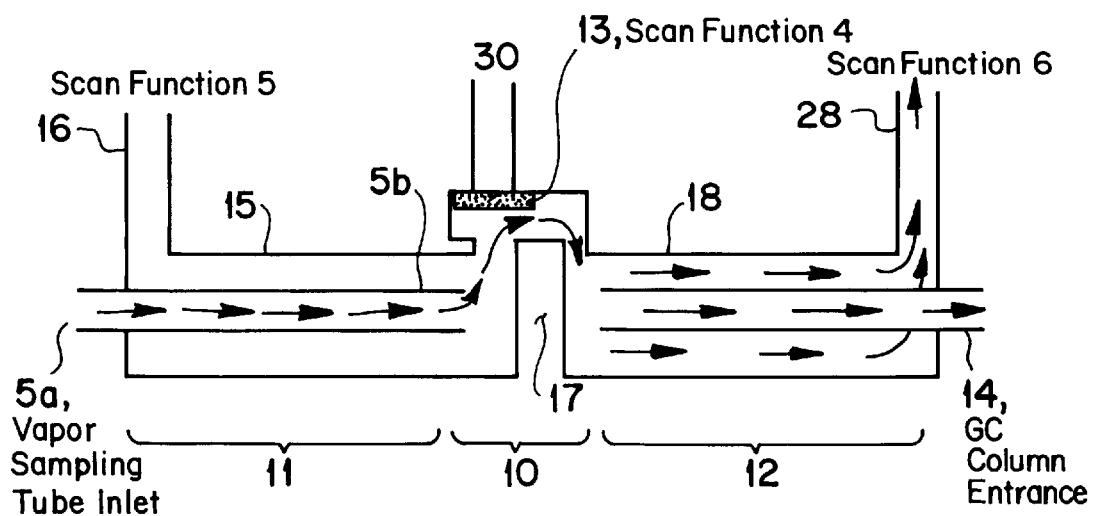

The three improvements in the macro 3-way valve make the modified macro 3-way valve 10 equivalent to a small volume micro valve without the disadvantages of a genuine micro-valve. The disadvantages of a micro-valve are high airflow resistance, easily clogged with particulate, and small connecting fittings that make it very difficult to service and very costly to manufacture. FIGS. 5A–B show a schematic presentation of a modified macro 3-way valve 10. FIG. 5A shows the modified macro 3-way valve 10 in the standby mode where scan function 4, activates the valve 13 into the closed position. Scan function 5, of the inlet interface 11 is set to allow clean dry air to flush and clean the internal surfaces in the inlet branch 15 of the 3-way valve. Scan function 6, which controls the airflow through the outlet interface 12, is set to allow clean dry air to flush and clean the internal volumes/surfaces of the modified macro 3-way valve 10 and outlet interface 12. FIG. 5B shows the modified macro 3-way valve 10 in the sample injection mode where the valve 13 is in the open position. Scan function 5, which controls the airflow through the inlet branch airflow entrance 16 of the inlet branch 15 of the inlet interface 11, is in the closed position where no clean dry air is flowing through the inlet branch 15. Scan function 6, controls the airflow of the outlet interface 12 through the 3-way valve 10 and is set to a preferred very low flow rate of 1 ml/min. The distance between the vapor sampling tube outlet 5b and the modified macro 3-way valve orifice wall 17 was minimized, and the distance between the GC column inlet 14 and the 3-way valve orifice wall 17 was minimized. Distances are set in a way to permit maximum transmission of vapor products, and to minimize the dilution volume. Various distances (0.1–25 mm) were investigated for both interfaces, and the preferred distance is 2 mm between the vapor sampling tube outlet 5b and the 3-way valve orifice wall 17 and between the inlet of the GC column 14 and the 3-way valve orifice wall 17. The volume of the 3-way valve inlet branch 15 is 75 ul and the volume of the outlet branch 18 is 75 ul. Diffusion of the sample vapor can occur in this 150 ul of volume. However, when the airflow scan function 5, is turned off (inactivated), valve 13 is opened, and airflow scan function 6, is activated, the sample vapor flow is entrained in such a way that the volume between the vapor sampling tube outlet 5b and the entrance 14 of the GC column 14 is in the low nanoliter range.

Figure 7:
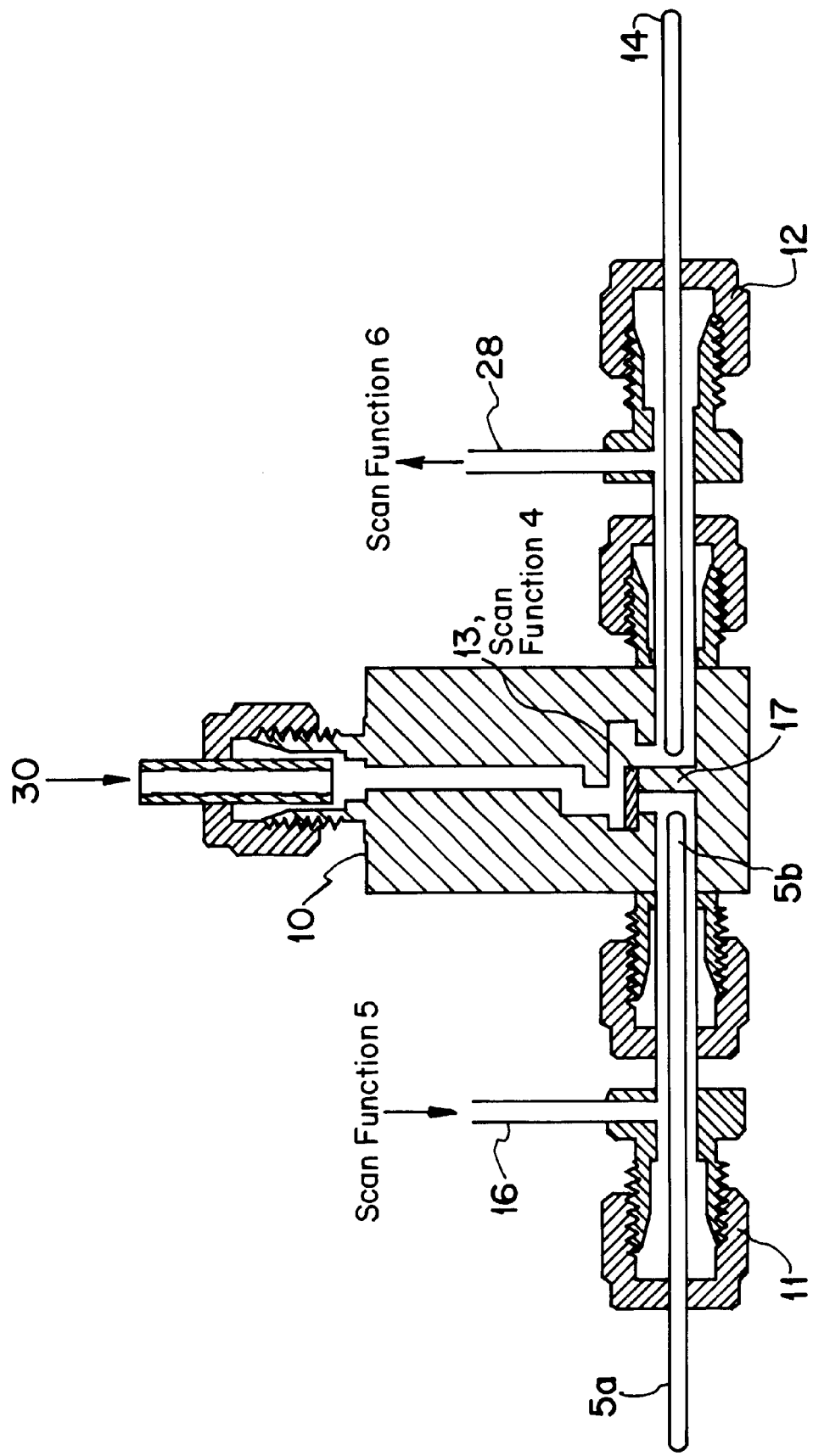
FIG. 7 is a schematic representation of the sample tube outlet and GC inlet interface to the injection valve.

The schematic in FIG. 5 of the inlet interface, outlet interface and the injection valve is represented as a "filled in" diagram in FIG. 7.

Figure 8:
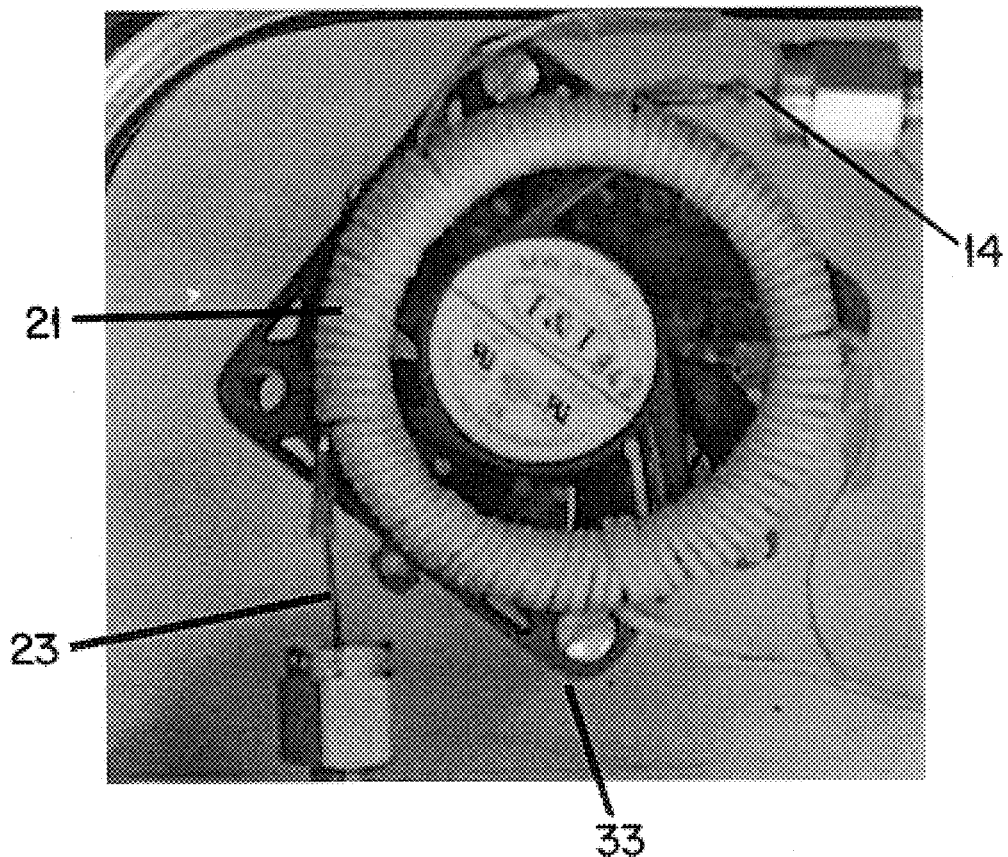
FIG. 8 is a photograph of the GC ring assembly with cooling fan shown below the GC ring.
Figure 9A:
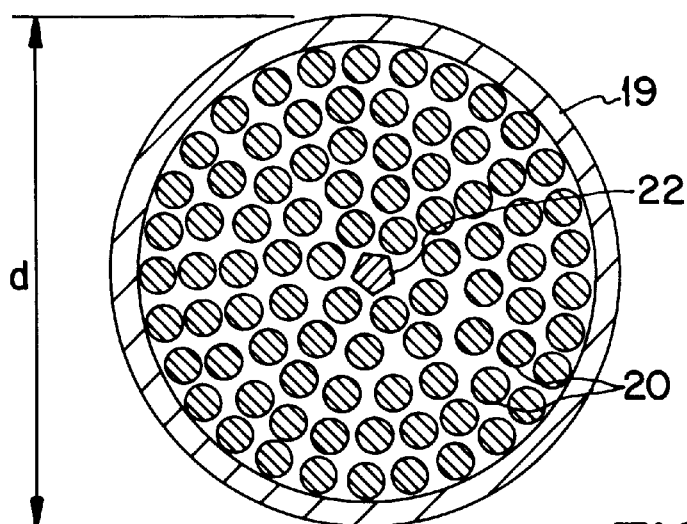
FIG. 9A is a cross section of the modified ring-shaped temperature-programmable GC assembly.

FIG. 8 shows a digital picture of the GC/heating assembly as it is situated in the BCS device. Note the entrance 14 and exit 23 of the GC assembly. A temperature sensing thermocouple wire is wound to form a single loop of thermocouple wire 22 (FIG. 9A). Each end of the wire is connected to an electronic circuit that converts the temperature-induced electrical current to a digital output. The continuous capillary GC column is repeatedly wound in a circular/toroidal manner such that the thermocouple loop resides in the center of the GC column windings (FIG. 9A). The GC column ring 21 is covered by a continuously wound heating wire jacket 19. This provides the heat to the GC capillary column.

Figure 9B:
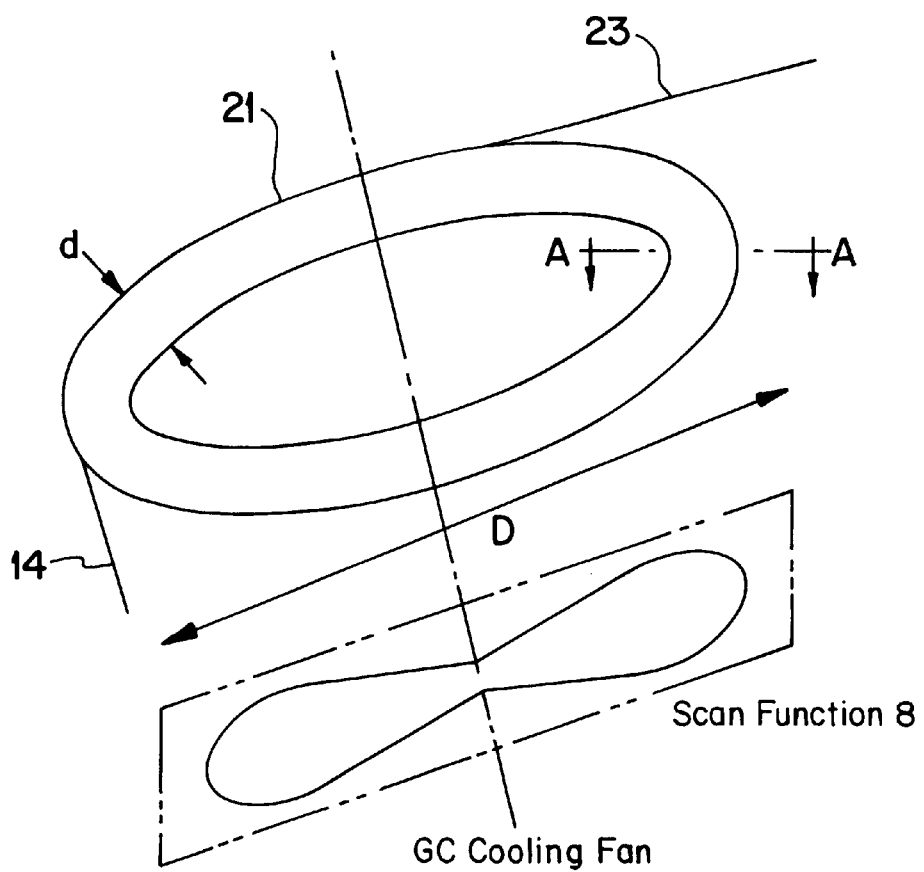
FIG. 9B is a schematic representation of a ring-shaped programmable GC assembly used in the BCS system.

The GC column/heating assembly is in the form of a ring or doughnut-shaped configuration, as shown in FIG. 9B.

There exists a relationship between the GC column/heating assembly outside diameter (D), as shown in FIG. 9b, and its cross-section outside diameter (d), as shown in FIGS. 9a,b. The shape of the GC column windings is adjusted in the D and d dimensions (FIG. 10) so that a uniform and rapid transfer of heat is imposed on the GC column when the GC column is heated from a low to a high temperature. The heating jacket 19 around the GC column ring 21 should be as thin as possible with minimal thermal mass capacity as well as high thermal conductivity. The GC column windings should generate a high-density number of column windings in the cross-sectional area (FIG. 9A). The GC column ring 21 should be coated (outside) with a reasonable thickness of high thermal conductivity (e.g., aluminum) coating 20 that eliminates any small temperature gradients between column windings. A temperature measurement thermocouple 22 (FIG. 9A) was placed in the center of the entire GC column ring 21.

Figure 10A:
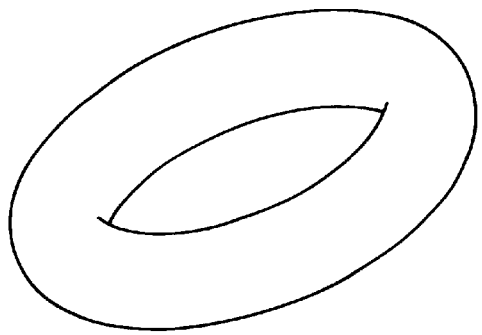
FIGS. 10A–C are schematic representations of three ring-shaped programmable GC assemblies showing various ratios of dimensions.
Figure 10B:
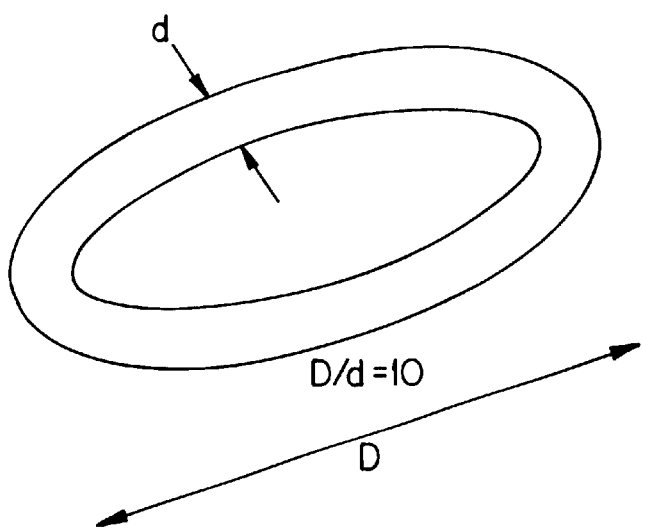
Figure 10C:
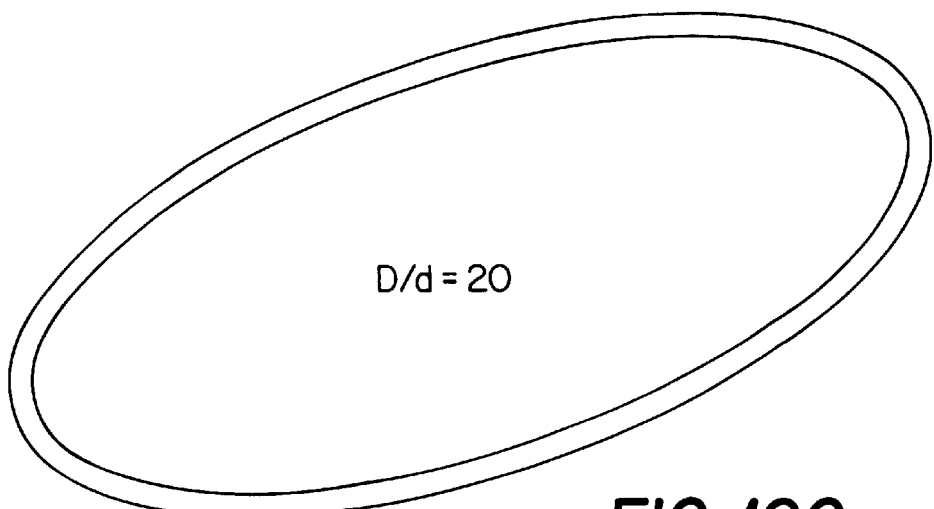

Various ratios of D/d (5–1000) were tested and the preferred ratio of 10 is used for the size/type of the GC column in the BCS system. This value produces the optimum, rapid heating and cooling rates for the ring-shaped GC and also happens to confer the best structural rigidity properties (FIG. 10). The latter property gives ruggedness to the GC in terms of longevity and support. This is an improvement over the GC system described in U.S. Pat. No. 5,856,616 (Hand-held temperature programmable modular gas chromatograph, inventors are Waleed M. Maswadeh and A. Peter Snyder; Jan. 5, 1999), because the size and diameter of the GC column ring 21 was neither specified nor optimized in the patent.

Various GC column types were tested and the preferred GC column that has optimum rigidity, vibration resistance, and temperature uniformity is the high temperature, Ultra Alloy Stainless Steel GC column (0.5 mm ID×0.15 um methyl silicone, Quadrex Corp., New Haven, Conn. 06525). The ring-shaped GC column assembly in U.S. Pat. No. 5,856,616 was improved (FIGS. 8 and 9B) for greater rigidity for the outdoor applications of the BCS system. As related in U.S. Pat. No. 5,856,616, the best (ideal) configuration for the GC column assembly is the ring shape. FIG. 10 shows various designs of a ring-shaped GC under different D/d ratios, and the improvement to the U.S. Pat. No. 5,856,616 was a D/d ratio of 10 for the ring-shaped GC column 21.

The design of the interface between the GC and the PC is shown in FIG. 11 and is described as follows: GC outlet-PC cell interface flange 32; electrical and thermal isolation between the high temperature GC exit 23 and PC front end 24. The GC exit 23 is placed close to the PC ionization region 26 in order to allow the PC internal airflow to direct the vapor sample that elutes out of the GC column exit 23 and into the ionization region 26 in FIG. 11 of the PC. The GC exit 23 is heated to the end of the column (to point "a") to ensure the eluting compounds experience minimum or no condensation and are quickly ionized by the ionization region before further cooling. The outlet branch airflow exit tube 28 provides the sweep airflow 25, and the PC cell pressure port 31 accesses a vacuum pump to provide a reduced pressure in the PC cell. The interface flange 32 is very critical and plays a significant part in GC resolution and sensitivity.

This is the first time that a temperature-programmed GC column ring 21 was heated all the way to the elution tip exit 23 and eluted into the room temperature region of a detector without condensation of the sample vapor or cold spots in the GC column. The sweep airflow 25 in FIG. 11 funnels and entrains the sample vapor through point "a" and into the ionization region 26 of the PC detector.

The interface 32 between the GC and the PC consists of a thermally insulated flange (ceramic is preferred) that makes an airtight connection between the PC front end (normally 10° C. above room temperature) and the high temperature GC outlet (preferred temperature value of 170° C.). The GC exit 23 is positioned to allow the eluting sample vapors from the GC column ring 21 to be in the center of PC ionization region 26 and to be funneled by the PC internal air flows as shown in FIG. 11.

Figure 6:
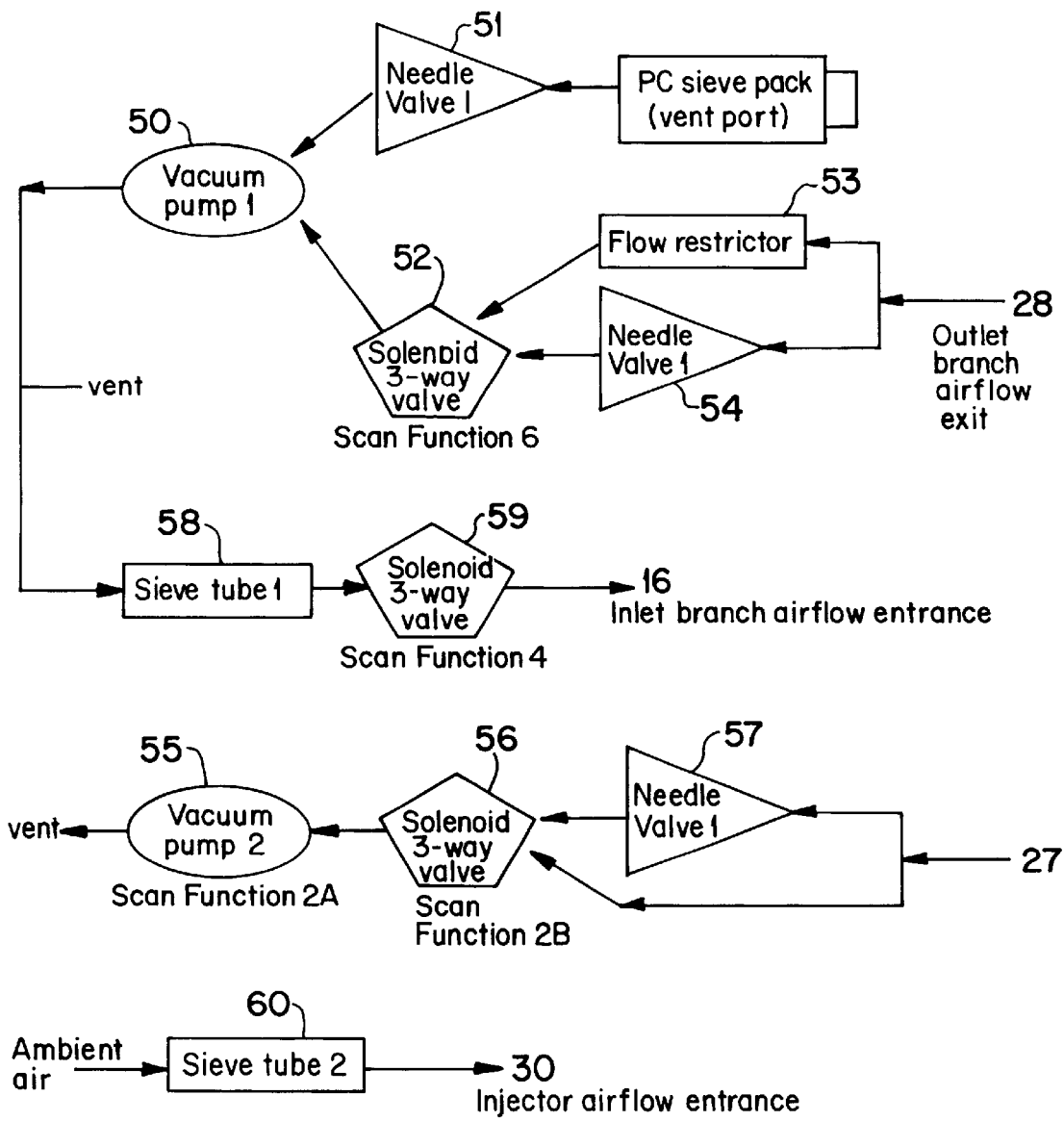
FIG. 6 is diagram of an airflow plumbing design used in the Biological Classifier System of the invention.

FIG. 6 shows the detailed air flow/switching/scrubbing plumbing design used in the BCS.

Two pumps are the preferred number of pumps to operate all the airflows in a dual analytical instrument the BCS system where reduced pressures are required. Maximal use is made of a minimum of two pumps.

Two separate vacuum pumps were integrated to drive the airflows over multiple regions in the system. The plumbing design and the switching airflow time profile are unique which integrate the entire system. The design was separated into individual modules. The vacuum pump module consists of reference numbers 50 to 57. The clean air-scrubbing module consists of parts 58 to 60. The individual parts of each module were fabricated to form the most compact module. Each module is easily replaceable.

The airflow network design features can be summarized as follows:

1. Automatic cleaning of internal surfaces by airflows.
2. Rapid change in flow rates; fast switching of flow rates from low to high and high to low.
3. Modular units for ease of replacement.
4. Integrated design to make maximum operation with only two vacuum pumps.

The PC system is a commercially available item. The standard system has a manual ON/OFF button.

The manual ON/OFF button in the PC system was removed and designed to be computer-operated with custom computer-controlled software.

The entire system is computer controlled by various scan functions as indicated above. More specifically, scan functions 1–8 are as follows:

Scan function 1: This controls the ON/OFF status of heating element (coiled wire) 6 at the appropriate time.

Scan function 3: This controls the cooling fan 7 that is used to cool down the sample-heating region covered by the heating element wire 6.

Scan function 2: This controls the flow rate through the quartz filter 3/quartz frit 4 and the sampling tube 5a at the appropriate time by turning ON/OFF 55 and 56 in FIG. 6.

Scan function 4: Controls the ON/OFF status of the injection valve 10 and valve 59.

Scan function 5: This controls the flow rate through the injection valve inlet port 11 region in FIG. 5.

Scan function 6: This controls the flow rate through the injection valve outlet port 12 and into port 28, in FIG. 5, by means of turning ON/OFF 52 in FIG. 6.

Scan function 7: This controls the temperature and the heating rate of the ring-shaped GC assembly 21 in FIG. 8.

Scan function 8: This controls the GC cooling fan 33 to quickly cool the ring-shaped GC to room temperature.

FIGS. 12 and 13 show typical BCS data that were collected for a mixture of three phosphonates in water (FIG. 12) and outdoor *Bacillus subtilis* spore (BG) aerosols (FIG. 13).

The PC device is continuously generating a signal array in an average of 20 signal arrays per second. Individual signal array consists of a PC response within a 0.02 second (20 millisecond) from the PC gate signal. Each horizontal line in FIG. 12 and FIG. 13 present an individual PC signal array. The GC device function is to separate individual compounds of the injected sample mixture in time (seconds frame). When the GC device is coupled with the PC device, the PC device will generate various signal arrays during the GC separation time (typically less than 60 seconds). The set of PC signal arrays in GC time is presented by the horizontal lines stacked in the y-axis according to the GC separation time. FIG. 12 and FIG. 13 consists of pixels where the horizontal pixels present an individual PC signal array and the y-axis presents the various PC signal array signatures of various separated compounds.

The BCS system is controlled by the use of computer program that was in-house written. The function of the program is to acquire the PC signal arrays in an average of 5 PC signal arrays per seconds and display them as shown in FIGS. 12 and 13 (counter format). FIG. 12 shows that DMMP has a strong signature intensity around 6.9 milliseconds in the PC signal array and separated/eluted around 7 seconds. Pixel intensity changes from white to red as the PC signal increases by the presence of compound.

In FIG. 13, a signal is observed that originates from picolinic acid (PA). PA is contained in the bacterial spore, and this is detailed in the open literature (58,63). There are open literature reports that provide a more detailed discussion of the BCS performance (60–62).

The improvements over prior Biological Classifier systems are:

The heating wire is wound in a certain configuration around the TD heating tube.

Pore size and frit thickness are optimized at 200 micrometers and 1 millimeter, respectively, for maximal transfer of the vapor to the modified macro 3-way injector entrance.

The position of the vapor sampling tube (entrance to the modified macro 3-way injector) to the quartz frit is optimized at 2 millimeters.

The airflow rate through the TD tube is optimized at 10 ml/min. The vapor is injected into the 3-way valve 4 seconds after the initiation of the heating event and the injection pulse spans an absolute time of 2 seconds. The flow rate of the sample into the vapor sampling tube is 27 ml/min. Another improvement is the modification of the macro 3-way injection valve to perform as a genuine micro 3-way injection valve.

The sample flow entering the GC column entrance is optimized when one part of the sample vapor enters the GC column and nine parts of sample vapor goes to the waste airflow. This 9:1 split of the sample vapor allows for a maximal clear-down time and minimal memory effects. The GC column dimensions are of a D/d=10. This is the first time that a temperature-programmed GC column is heated all the way to the tip (outlet) and elute into the room temperature region of a detector without condensation of the sample vapor on the GC column near the GC outlet region.

Two airflow pumps are all that is required to operate the airflows of the entire system.

The manual ON/OFF button in the PC detector was removed and designed to be computer-operated with custom computer-controlled software.

REFERENCES

1. W. D. Griffiths and G. A. L. DeCosemo, "The Assessment of Bioaerosols: A Critical Review," *J. Aerosol Sci.* 25, 1425–1458, (1994).
2. T. J. Mukoda, L. A. Todd and M. D. Sobsey, "PCR and Gene Probes for Detecting Bioaerosols," *J. Aerosol Sci.* 25, 1523–1532, (1994).
3. R. Leuschner, "Comparison of Airborne Pollen Levels in Switzerland at Four Recording Stations in Davos, Lucerne, Nyon and Basle During 1989," *Int. J. Biometeorology* 35, 71–75, (1991).
4. B. Crook and J. L. Sherwood-Higham, "Sampling and Assay of Bioaerosols in the Work Environment," *J. Aerosol Sci.* 28, 417–426, (1997).
5. P. G. Nugent, J. Cornett, I. W. Stewart and H. C. Parkes, "Personal Monitoring of Exposure to Genetically Modified Microorganisms in Bioaerosols: Rapid and Sensitive Detection Using PCR," *J. Aerosol Sci.* 28, 525–538, (1997).
6. J. Ho, "Is There Life in Arizona Road Dust? Point and Remote Biological Aerosol Measurement," *J. Aerosol Sci.* 23, S643–S646, (1992).
7. S. Laitinen, A. Nevalainen, M. Kotimaa, J. Liesivuori and P. J. Martikainen, "Relationship Between Bacterial Counts and Endotoxin Concentrations in the Air of Wastewater Treatment Plants," *Appl. Environ. Microbiol.* 58, 3774–3776, (1992).
8. I. W. Stewart, G. Leaver and S. J. Futter, "The Enumeration of Aerosolised *Saccharomyces cerevisiae* Using Bioluminescent Assay of Total Adenylates," *J. Aerosol Sci.* 28, 511–523, (1997).
9. S. E. Speight, B. A. Hallis, A. M. Bennett and J. E. Benbough, "Enzyme-Linked Immunosorbent Assay for the Detection of Airborne Microorganisms Used in Biotechnology," *J. Aerosol Sci.* 28, 483–492, (1997).
10. M. W. Thompson, J. Donnelly, S. A. Grinshpun, A. Juozaitis and K. Willeke, "Method and Test System for Evaluation of Bioaerosol Samplers," *J. Aerosol Sci.* 25, 1579–1593, (1994).
11. U. Seydel and B. Lindner, "Qualitative and Quantitative Investigations on Mycobacteria with LAMMA," *Fresenius Z. Anal. Chem.* 308, 253–257, (1981).
12. U. Seydel and B. Lindner, "Monitoring of Bacterial Drug Response by Mass Spectrometry of Single Cells," *Biomed. Environ. Mass Spectrom.* 16, 457–459, (1988).
13. R. Bohm, "Sample Preparation Technique for the Analysis of Vegetative Bacteria Cells of the Genus Bacillus with the Laser Microprobe Mass Analyzer (LAMMA)," *Fresenius Z. Anal. Chem.* 308, 258–259, (1981).
14. R. Bohm, T. Kapr and H. U. Schmitt, "Application of the Laser Microprobe Mass Analyser (LAMMA) to the Differentiation of Single Bacterial Cells," *J. Anal. Appl. Pyrolysis* 8, 449–461, (1985).
15. L. Van Vaeck, J. Claereboudt, J. De Waele, E. Esmans and R. Gijbels, "Approach for Structural Interpretation of Laser Microprobe Mass Spectra of Organic Compounds," *Anal. Chem.* 57, 2944–2951, (1985).
16. P. Wieser, R. Wurster and U. Haas, "Application of LAMMA in Aerosol Research," *Fresenius Z. Anal. Chem.* 308, 260–269, (1981).
17. L. Van Vaeck, H. Struyf, W. Van Roy and F. Adams, "Organic and Inorganic Analysis with Laser Microprobe Mass Spectrometry. Part I: Instrumentation and Methodology," *Mass Spectrom. Rev.* 13, 189–208, (1994).
18. L. Van Vaeck, H. Struyf, W. Van Roy and F. Adams, "Organic and Inorganic Analysis with Laser Microprobe Mass Spectrometry. Part II: Applications," *Mass Spectrom. Rev.* 13, 209–232, (1994).
19. M. P. Sinha, C. E. Giffin, D. D. Norris, T. J. Estes, V. L. Vilker and S. K. Friedlander, "Particle Analysis by Mass Spectrometry," *J. Colloid Interface Sci.* 87, 140–153, (1982).
20. M. P. Sinha, R. M. Platz, V. L. Vilker, S. K. Friedlander, "Analysis of Individual Biological Particles by Mass Spectrometry," *Intl. J. Mass Spectrom. Ion Processes* 57, 125–133, (1984).
21. M. P. Sinha, R. M. Platz, S. K. Friedlander and V. L. Vilker, "Characterization of Bacteria by Particle Beam Mass Spectrometry," *Appl. Environ. Microbiol.* 49, 1366–1373, (1985).
22. K. R. Spurny, "On the Chemical Detection of Bioaerosols," *J. Aerosol Sci.* 25, 1533–1547, (1994).
23. M. P. Sinha, "Laser-Induced Volatilization and Ionization of Microparticles," *Rev. Sci. Instrum.* 55, 886–891, (1984).
24. R. A. Gieray, P. T. A. Reilly, M. Yang, W. B. Whitten, J. M. Ramsey, "Real-Time Detection of Individual Airborne Bacteria," *J. Microbiol. Methods* 29, 191–199, (1997).
25. K. P. Hinz, R. Kaufmann and B. Spengler, "Laser-Induced Mass Analysis of Single Particles in the Airborne State," *Anal. Chem.* 66, 2071–2076, (1994).
26. K. P. Hinz, R. Kaufmann and B. Spengler, "Simultaneous Detection of Positive and Negative Ions From Single Airborne Particles by Real-Time Laser Mass Spectrometry," *Aerosol Sci. Technol.* 24, 233–242, (1996).
27. M. Yang, P. T. A. Reilly, K. B. Boraas, W. B. Whitten and J. M. Ramsey, "Real-Time Chemical Analysis of Aerosol Particles Using an Ion Trap Mass Spectrometer," *Rapid Commun. Mass Spectrom.* 10, 347–351, (1996).
28. W. Maswadeh, K. A. Roberts, W. H. McClennen, H. L. C. Meuzelaar and N. S. Arnold, "Laser Pyrolysis Mass Spectrometry of Single Levitated Coal Particles," paper presented at the 37$^{th}$ ASMS Conference on Mass Spectrometry and Allied Topics, Miami Beach, Fla., 1989, pp 304–305.
29. W. Maswadeh, N. S. Arnold and H. L. C. Meuzelaar, "Laser Pyrolysis-Transfer Line Chromatography/Mass Spectrometry of Single, Levitated Coal Particles," paper presented at the 38$^{th}$ ASMS Conference on Mass Spectrometry and Allied Topics, Tucson, Ariz., 1990, pp 599–600.
30. J. Marijnissen, B. Scarlett and P. Verheijen, "Proposed On-Line Aerosol Analysis Combining Size Determination, Laser-Induced Fragmentation and Time-Of-Flight Mass Spectroscopy," *J. Aerosol Sci.* 19, 1307–1310, (1988).
31. P. G. Carson, K. R. Neubauer, M. V. Johnston and A. S. Wexler, "On-Line Chemical Analysis of Aerosols by Rapid Single-Particle Mass Spectrometry," *J. Aerosol Sci.* 26, 535–545, (1995).
32. K. A. Prather, T. Nordmeyer and K. Salt, "Real-Time Characterization of Individual Aerosol Particles Using Time-Of-Flight Mass Spectrometry," *Anal. Chem.* 66, 1403–1407, (1994).
33. T. Nordmeyer and K. A. Prather, K. A., "Real-Time Measurement Capabilities Using Aerosol Time-Of-Flight Mass Spectrometry," *Anal. Chem.* 66, 3540–3542, (1994).
34. K. Salt, C. A. Noble and K. A. Prather, "Aerodynamic Particle Sizing Versus Light Scattering Intensity Measurement as Methods for Real-Time Particle Sizing Coupled with Time-Of-Flight Mass Spectrometry," *Anal. Chem.* 68, 230–234, (1996).
35. C. A. Noble and K. A. Prather, "Real-Time Measurement of Correlated Size and Composition Profiles of Individual Atmospheric Aerosol Particles," *Environ. Sci. Technol.* 30, 2667–2680, (1996).
36. P. J. Silva and K. A. Prather, "On-Line Characterization of Individual Particles from Automobile Emissions," *Environ. Sci. Technol.* 31, 3074–3080, (1997).
37. D. Y. Liu, D. Rutherford, M. Kinsey and K. A. Prather, "Real-Time Monitoring of Pyrotechnically Derived Aerosol Particles in the Troposphere," *Anal. Chem.* 69, 1808–1814, (1997).
38. E. Gard, J. E. Mayer, B. D. Morrical, T. Dienes, D. P. Fergenson, and K. A. Prather, "Real-Time Analysis of Individual Atmospheric Aerosol Particles: Design and Performance of a Portable ATOFMS," *Anal. Chem.* 69, 4083–4091, (1997).
39. E. E. Gard, M. J. Kleeman, D. S. Gross, L. S. Hughes, J. O. Allen, B. D. Morrical, D. P. Fergenson, T. Dienes, M. E. Galli, R. J. Johnson, G. R. Cass and K. A. Prather, "Direct Observation of Heterogeneous Chemistry in the Atmosphere," *Science* 279, 1184–1187, (1998).
40. A. Fox, L. Wright, and K. Fox, "Gas Chromatography-Tandem Mass Spectrometry for Trace Detection of Muramic Acid, a Peptidoglycan Marker, in Organic Dust," *J. Microbiol. Methods* 22,11–26, (1995).
41. A. Fox and R. M. T. Rosano, "Quantification of Muramic Acid, a Marker for Bacterial Peptidoglycan, in Dust collected from Home and Hospital Air-Conditioning Filters using Gas Chromatography-Mass Spectrometry," *Indoor Air* 4, 239–247, (1994).
42. A. Fox, M. Krahmer and D. Harrelson, "Monitoring Muramic Acid in Air (after Alditol Acetate Derivatization) using a Gas Chromatograph-Ion Trap Mass Spectrometer," *J. Microbiol. Methods* 27, 129–138, (1996).
43. A. Saraf, L. Larsson, H. Burge and D. Milton "Quantification of Ergosterol and 3-Hydroxy Fatty Acids in Settled House Dust by Gas Chromatography-Mass Spectrometry: Comparison with Fungal Culture and Determination of Endotoxin by a Limulus Amebocyte Lysate Assay," *Appl. Environ. Microbiol.* 63, 2554–2559; (1997).
44. A. Saraf and L. Larsson, "Use of Gas Chromatography/Ion Trap Mass Spectrometry for Determination of Chemical Markers of Microorganisms in Organic Dust," *J. Mass Spectrom.* 31, 389–396, (1996).
45. I. Elmroth, A. Valeur, G. Odham and L. Larsson, "Detection of Microbial Contamination in Fermentation Processes: Mass Spectrometric Determination of Gram-Negative Bacteria in Leuconostoc mesenteroides Culture," *Biotechnol. Bioeng.* 35, 787–792, (1990).
46. I. Elmroth, P. Sundin, A. Valeur, L. Larsson and G. Odham, "Evaluation of Chromatographic Methods for the Detection of Bacterial Contamination in Biotechnical Processes," *J. Microbiol. Methods* 15, 215–228, (1992).
47. B. T. N. Evans, E. Yee, G. Roy and J. Ho, "Remote Detection and Mapping of Bioaerosols," *J. Aerosol Sci.* 25, 1549–1566, (1994).
48. R. G. Pinnick, S. C. Hill, P. Nachman, J. D. Pendleton, G. L. Fernandez, M. W. Mayo and J. G. Bruno, "Fluorescence Particle Counter for Detecting Airborne Bacteria and Other Biological Particles," *Aerosol Sci. Technol.* 23, 653–664, (1995).
49. P. Nachman, G. Chen, R. G. Pinnick, S. C. Hill, R. K. Chang, M. W. Mayo, and G. L. Fernandez, "Conditional-Sampling Spectrograph Detection System for Fluorescence Measurements of Individual Airborne Biological Particles," *Appl. Optics* 35, 1069–1076, (1996).
50. R. G. Pinnick, S. C. Hill, P. Nachman, G. Videen, G. Chen and R. K. Chang, "Aerosol Fluorescence Spectrum Analyzer for Rapid Measurement of Single Micrometer-Sized Airborne Biological Particles," *Aerosol Sci. Technol.* 28, 95–104, (1998).
51. P. P. Hairston, J. Ho and F. R. Quant, "Design of an Instrument for Real-Time Detection of Bioaerosols Using Simultaneous Measurement of Particle Aerodynamic Size and Intrinsic Fluorescence," *J. Aerosol Sci.* 28, 471–482, (1997).
52. H. L. C. Meuzelaar, M. G. Kim, N. S. Arnold, P. Kalousek, A. P. Snyder, "Hand-Portable Gas Chromatography/Ion Mobility Spectrometry; The "Poor Man's" CB Detection System?" Proceedings of the ARO 1991 Workshop on Spectrometry and Spectroscopy for Biologicals, Cashiers, N.C., 38–48, (1991).
53. S. N. Thornton, J. P. Dworzanski, H. L. C. Meuzelaar, W. M. Maswadeh, A. P. Snyder "Pyrolysis-Gas Chromatography/Ion Mobility Spectrometry Detection of Dipicolinic acid biomarker in *Bacillus subtilis* Spores during Field Bioaerosol Releases," Proceedings from the 1997 Field Analytical Methods for Hazardous Waste and Toxic Chemicals, Las Vegas, Nev., 802–811, (1997).
54. S. N. Thornton, "Chemical Markers in Bacterial Spores and Potential Background Aerosols by Pyrolysis-Gas Chromatography/Ion Mobility Spectrometry" Ph.D. Thesis, University of Utah, (1999).
55. A. P. Snyder, C. S. Harden, A. H. Brittain, M.-G. Kim, N. S. Arnold and H. L. C. Meuzelaar, "Portable, Hand-Held Gas Chromatography-Ion Mobility Spectrometer," *Am. Lab.* 24, 32 B-H, (1992).
56. A. P. Snyder, C. S. Harden, A. H. Brittain, M. G. Kim, N. S. Arnold and H. L. C. Meuzelaar, "Portable Hand-Held Gas Chromatography/Ion Mobility Spectrometry Device," *Anal. Chem.* 65, 299–306, (1993).
57. J. P. Dworzanski, M. G. Kim, A. P. Snyder, N. S. Arnold and H. L. C. Meuzelaar, "Performance Advances in Ion Mobility Spectrometry Through Combination with High Speed Vapor Sampling, Preconcentration and Separation Techniques," *Anal. Chim. Acta* 293, 219–235, (1994).
58. A. P. Snyder, S. N. Thornton, J. P. Dworzanski and H. L. C. Meuzelaar, "Detection of the Picolinic Acid Biomarker in Bacillus Spores Using a Potentially Field-Portable Pyrolysis-Gas Chromatography-Ion Mobility Spectrometry System," *Field Anal. Chem. Technol.* 1, 49–58, (1996).
59. J. P. Dworzanski, W. H. McClennen, P. A. Cole, S. N. Thornton, H. L. C. Meuzelaar, N. S. Arnold and A. P. Snyder, "Field-Portable, Automated Pyrolysis-GC/IMS System for Rapid Biomarker Detection in Aerosols: A Feasibility Study", Field Anal. Chem. Technol. 1, 295–305, (1997).
60. A. Peter Snyder, Waleed M. Maswadeh, John A. Parsons, Ashish Tripathi, Henk L. C. Meuzelaar, Jacek P. Dworzanski and Man-Goo Kim "Field detection of bacillus spore aerosols with stand-alone Py-GC-IMS" Field Anal. Chem. Technol. 3 (1999) 315–326.
61. A. Peter Snyder, Waleed M. Maswadeh, Ashish Tripathi and Jacek P. Dworzanski "Detection of Gram negative *Erwinia herbicola* outdoor aerosols with Py-GC-IMS" Field Anal. Chem. Technol. 4 (2000) 111–126.
62. A. Peter Snyder, Ashish Tripathi, Waleed M. Maswadeh, Jim Ho and Mel Spence "Field detection and identification of a bioaerosol suite by Py-GC-IMS" Field Anal. Chem. Technol. 5 (2001) 190–204.
63. G. W. Gould and A. Hurst, Eds., The Bacterial Spore, Academic Press, New York, N.Y., 1969.

What is claimed is:

1. A biological classification system, comprising:
a thermal decomposition tube for processing a biological sample and producing a resultant vapor;
wherein said thermal decomposition tube comprises:
an elongated tube having a first side with an entrance and a second side with an exit;
an interface housing supporting said second side of said elongated tube;
a microfiber filter positioned within said tube across the diameter of said tube to separate said first side from said second side, and wherein a quartz frit is permanently fixed juxtapose to the microfiber filter in the second side of said tube;
an elongated vapor sampling tube positioned inside said thermal decomposition tube, said vapor sampling tube having an entrance end and an exit end, said vapor sampling tube held in place at the exit end by said interface housing, wherein said exit end extends to an outside of said interface housing, said entrance end positioned a distance D from said quartz frit;
a heating element wrapped around an outer circumference of said elongated tube for causing a heated region;
a cooling fan assembly for cooling the heated region; and
a tube vent in said interface housing;
a gas chromatography module interfaced with said thermal decomposition tube by a three-way injection valve, said gas chromatography module for receiving said resultant vapor from said thermal decomposition tube;
and a plasma chromatograph vapor detector interfaced via a GC/PC interface with said gas chromatography module for receiving resultant vapor from said gas chromatography module; wherein said thermal decomposition tube, said gas chromatography module and said plasma chromatograph vapor detector are connected in series for separation, isolation and classification of individual components from the thermal decomposition of biological analytes introduced into the thermal decomposition tube.

2. A biological classification system, comprising:
a thermal decomposition tube for processing a biological sample and producing a resultant vapor;
a gas chromatography module interfaced with said thermal decomposition tube by a three-way injection valve, said gas chromatography module for receiving said resultant vapor from said thermal decomposition tube;
wherein the gas chromatography module comprises:
a GC column ring structure comprising a continuous capillary column repeatedly wound in a direction transverse to the direction of the ring structure in a toroidal manner; said capillary column having an entrance end and an exit end;
a temperature sensing thermocouple wire connected to an electronic circuit for converting a temperature-induced electrical current to a digital output, said thermocouple wire residing inside the capillary column windings, forming a single wire ring inside of said ring structure;
a heating wire jacket around said ring structure for providing heat to the GC column; and
a GC cooling fan;
and a plasma chromatograph vapor detector interfaced via a GC/PC interface with said gas chromatography module for receiving resultant vapor from said gas chromatography module;
wherein said thermal decomposition tube, said gas chromatography module and said plasma chromatograph vapor detector are connected in series for separation, isolation and classification of individual components from the thermal decomposition of biological analytes introduced into the thermal decomposition tube.

3. The system of claim 1 or 2, wherein said thermal decomposition tube comprises a quartz tube thermal decomposition tube.

4. The system of claim 1 or 2, wherein said biological analytes comprise biological substances selected from the group consisting of Gram-positive Bacillus spores, Gram-negative vegetative organisms and proteins.

5. The system of claim 1 or 2, wherein said system detects the presence of ambient biological and chemical aerosols from an aerosol concentrator.

6. The system of claim 1 or 2, wherein said system accepts and detects biological and chemical substances in liquid matrices by syringe injection into the system at the location of the thermal decomposition tube.

7. The system of claim 1 or 2, wherein said system accepts and detects vapors and gases by direct introduction into the thermal decomposition tube.

8. The system of claim 1, wherein sample is introduced into the entrance of said first side of the thermal decomposition tube and solids are deposited and vapors pass through the micro fiber filter.

9. The system of claim 1 or 2, wherein said thermal decomposition tube is Pyrex®.

10. The system of claim 1 or 2, wherein said thermal decomposition tube is ¼ inch outer diameter×4 mm inner diameter×50 mm long.

11. The system of claim 1, wherein the filter is a high-temperature aerosol retaining filter.

12. The system of claim 1, wherein said filter is a quartz micro-fiber filter.

13. The system of claim 1, wherein said filter is replaceable.

14. The system of claim 1, wherein said vapor sampling tube comprises a fused silica glass-lined stainless steel tube.

15. The system of claim 1, wherein said vapor sampling tube is 1/16 inch outer diameter and×0.02 inch inner diameter×3.65 inch long.

16. The system of claim 1, wherein said elongated tube is an inert glass material.

17. The system of claim 1, wherein said distance D between said vapor sampling tube entrance and said quartz frit is about 2 mm.

18. The system of claim 1, wherein said quartz frit has an internal pore size of 200 microns and a thickness of about 1 mm.

19. The system of claim 1, wherein said heating wire is a 0.013-inch outer diameter Alomega® wire with a low total thermal mass capacity and a heating rate that reaches 700 C. in 2–3 seconds.

20. The system of claim 1, wherein said heating wire is coiled in a manner where the coil winding density is higher about a region of the filter and frit than that about a region of the entrance of the vapor sampling tube.

21. The system of claim 1 or 2, further comprising a cooling fan assembly for cooling the thermal decomposition tube between analysis of successive samples.

22. The system of claim 1 or 2, wherein said three-way injection valve provides vapor sample injection into the gas chromatography module and comprises:

an inlet interface region for receiving said exit end of said vapor sampling tube of said thermal decomposition tube, said inlet interface region further having a airflow entrance; an outlet interface region for interfacing with said gas chromatography module at an entrance of said gas chromatography module, said outlet interface region further having an airflow exit;

an outlet branch airflow exit; and a valve region having an injector orifice valve between said inlet interface region and said outlet interface region of said three-way valve, said valve region further having an injector airflow inlet.

23. The system of claim 22, wherein a distance between the vapor sampling tube exit end and the injector orifice valve in said valve region is 2 mm.

24. The gas chromatography module of claim 2, wherein a relationship between the GC column ring structure outside diameter (D), and a GC column ring structure cross-section section outside diameter (d) is D/d, wherein the ration D/d is about 10, so that a uniform and rapid transfer of heat is imposed on the GC column when the GC column is heated from a low to a high temperature.

25. The gas chromatography module of claim 2, wherein said heating wire jacket has a high thermal coating conductivity for eliminating small temperature gradients between column windings.

26. The gas chromatography module of claim 2, wherein said heating wire jacket is aluminum.

27. The system of claim 2, wherein said GC/PC interface comprises:

an interface flange for providing an electrical and thermal isolation between the gas chromatography exit and a front end of said plasma chromatograph;

a plasma chromatograph ionization region in proximity to the gas chromatography exit at a region A;

a plasma chromatograph internal airflow for directing a vapor sample that elutes out of the gas chromatograph column exit into the ionization region;

an outlet branch airflow exit tube for providing a sweep airflow through said region A and directing the vapor sample through region A into the ionization region;

and a cell pressure port with a vacuum pump associated therewith to provide a reduced pressure in the plasma chromatography wherein said gas chromatography column ring is heated to the gas chromatography exit and said vapor sample is eluted into said room temperature region A without condensation of the vapor sample or cold spots in the gas chromatograph column.

28. The gas chromatograph of claim 2, wherein said gas chromatograph exit is heated to the end of the column for insuring that eluting compounds experience minimum or no condensation and are ionized by the ionization region before cooling.

29. The interface of claim 27, wherein said GC/PC interface comprises a thermally insulated flange.

30. The interface of claim 27, wherein said GC/PC interface flange is ceramic.

31. The system of claim 27, wherein said region A has a temperature of about 10° C. above room temperature and the exit of said gas chromatography module is about 170° C.

32. A biological classification system, comprising:

(A) a thermal decomposition tube for processing a biological sample and producing a resultant vapor, wherein said thermal decomposition tube comprises (a) an elongated tube having a first side with an entrance and a second side with an exit;

(b) an interface housing supporting said second side of said elongated tube;

(c) a microfiber filter positioned within said tube across the diameter of said tube to separate said first side from said second side, and wherein a quartz frit is permanently fixed juxtapose to the microfiber filter in the second side of said tube;

(d) an elongated vapor sampling tube positioned inside said thermal decomposition tube, said vapor sampling tube having an entrance end and an exit end, said vapor sampling tube held in place at the exit end by said interface housing, wherein said exit end extends to on outside of said interface housing, said entrance end positioned a distance D from said quartz frit;

(e) a plurality of heating wires wrapped around an outer circumference of said elongated tube; and (f) a tube vent in said interface housing;

(B) a gas chromatography module interfaced with said thermal decomposition tube by a three-way injection valve, said gas chromatography module for receiving said resultant vapor from said thermal decomposition tube, (aa) wherein said three-way injection valve provides vapor sample injection into the gas chromatography module and comprises:

(bb) an inlet interface region for receiving said exit end of said vapor sampling tube of said thermal decomposition tube, said inlet interface region further having a airflow entrance;

(cc) an outlet interface region for interfacing with said gas chromatography module at an entrance of said gas chromatography module, said outlet interface region further having an airflow exit; and (dd) a valve region having an injector orifice valve between said inlet interface region and said outlet interface region of said three-way valve, said valve region further having an injector airflow inlet, and wherein the gas chromatography module comprises:

(ee) a GC column ring structure comprising a continuous capillary column repeatedly wound in a direction transverse to the direction of the ring structure in a toroidal manner; said capillary column having an entrance end and an exit end;

(ff) a temperature sensing thermocouple wire connected to an electronic circuit for converting a temperature-induced electrical current to a digital output, said thermocouple wire residing inside the capillary column windings, forming a single wire ring inside of said ring structure;

(gg) a heating wire jacket around said ring structure for providing heat to the GC column; and (hh) a GC cooling fan; and (C) plasma chromatograph vapor detector interfaced via a GC/PC interface with said gas chromatography module for receiving resultant vapor from said gas chromatography module, wherein said GC/PC interface comprises (aaa) an interface flange for providing an electrical and thermal isolation between the gas chromatography exit and a front end of said plasma chromatograph;

(bbb) a plasma chromatograph ionization region in proximity to the gas chromatography exit at a region A;

(ccc) a plasma chromatograph internal airflow for directing a vapor sample that elutes out of the gas chromatograph column exit into the ionization region;

(ddd) an outlet branch airflow exit tube for providing a sweep airflow through said region A and directing the vapor sample through region A into the ionization region;

(eee) and a cell pressure port with a vacuum pump associated therewith to provide a reduced pressure in the plasma chromatograph, wherein said gas chromatography column ring is heated to the gas chromatography exit and said vapor sample is eluted into said room temperature region A without condensation of the vapor sample or cold spots in the gas chromatograph column; and wherein said thermal decomposition tube, said gas chromatography module and said plasma chromatograph vapor detector are connected in series for separation, isolation and classification of individual components from the thermal decomposition of biological analytes introduced into the thermal decomposition tube.

33. The system of claim 32, wherein during operation of said system, there are scan functions 1–8, wherein scan function 1 controls an On/Off status of said heating element of said thermal decomposition tube, wherein scan function 2 controls a flow rate through the filter and frit and the sampling elongated tube, wherein scan function 3 controls the cooling fan assembly for cooling the heated region, wherein scan function 4 controls an On/Off/status of the injection valve, wherein scan function 5 controls a flow rate through the injection valve inlet interface region, wherein scan function 6 controls the flow rate through the injection valve outlet interface and into said outlet branch airflow exit, wherein scan function 7 controls a temperature and heating rate of the GC column ring structure, and wherein scan function 8 controls the GC cooling fan to cool the ring shaped GC to room temperature.

* * * * *